(12) United States Patent
Buehrer et al.

(10) Patent No.: US 8,067,021 B2
(45) Date of Patent: Nov. 29, 2011

(54) METHODS AND COMPOSITIONS FOR DELIVERY OF GROWTH FACTOR TO FIBROUS CONNECTIVE TISSUE

(75) Inventors: Benjamin Marcus Buehrer, Chapel Hill, NC (US); Paul Hamilton, Cary, NC (US); Dalia Juzumiene, Cary, NC (US); Shrikumar Nair, Cary, NC (US); Yuchen Chen, Chapel Hill, NC (US)

(73) Assignee: Affinergy, Inc., Durham, NC (US)

( * ) Notice: Subject to any disclaimer, the term of this patent is extended or adjusted under 35 U.S.C. 154(b) by 447 days.

(21) Appl. No.: 12/204,731

(22) Filed: Sep. 4, 2008

(65) Prior Publication Data
US 2009/0098175 A1  Apr. 16, 2009

Related U.S. Application Data

(60) Provisional application No. 60/969,748, filed on Sep. 4, 2007.

(51) Int. Cl.
*A61F 13/00* (2006.01)
*A61K 38/00* (2006.01)
*A61K 38/18* (2006.01)
*A61K 38/10* (2006.01)
*A61K 38/16* (2006.01)
*C07K 14/475* (2006.01)

(52) U.S. Cl. .......... 424/422; 514/1.1; 514/7.6; 514/21.4

(58) Field of Classification Search .................. None
See application file for complete search history.

(56) References Cited

U.S. PATENT DOCUMENTS

| | | | |
|---|---|---|---|
| 5,908,828 A * | 6/1999 | Kurita et al. .................. 514/8.8 |
| 7,208,011 B2 | 4/2007 | Shanley et al. |
| 7,238,669 B2 | 7/2007 | Bishop-Hurley et al. |
| 7,252,832 B1 | 8/2007 | Stone et al. |
| 2002/0012652 A1 | 1/2002 | Levy |
| 2002/0151708 A1 | 10/2002 | Guerriero |
| 2003/0185870 A1 * | 10/2003 | Grinstaff et al. ............. 424/423 |
| 2004/0127640 A1 | 7/2004 | Belcher |
| 2005/0208095 A1 | 9/2005 | Hunter |
| 2006/0051395 A1 | 3/2006 | Beyer |
| 2006/0123505 A1 | 6/2006 | Kikuchi et al. |
| 2006/0147438 A1 | 7/2006 | Azevedo et al. |
| 2006/0233747 A1 | 10/2006 | Kochendoerfer |
| 2007/0077267 A1 | 4/2007 | Molz, IV et al. |
| 2007/0104758 A1 | 5/2007 | Hamilton et al. |
| 2007/0160644 A1 | 7/2007 | Kenan et al. |
| 2008/0268015 A1 | 10/2008 | Gron |
| 2011/0117165 A1 * | 5/2011 | Melican et al. ............... 424/423 |
| 2011/0117166 A1 * | 5/2011 | Melican ........................ 424/423 |
| 2011/0117167 A1 * | 5/2011 | Sanford et al. ............... 424/423 |
| 2011/0117168 A1 * | 5/2011 | Sathya et al. ................. 424/423 |

FOREIGN PATENT DOCUMENTS

| | | | |
|---|---|---|---|
| WO | W09528832 A1 | | 11/1995 |
| WO | WO 00/36081 | * | 6/2000 |
| WO | WO2009/018484 | | 2/2009 |
| WO | WO2009/120968 | | 10/2009 |

OTHER PUBLICATIONS

H.J.C. Berendsen. A Glimpse of the Holy Grail? Science (1998) 282, pp. 642-643.*
Rudinger. In: Peptide Hormones, JA Parsons, Ed. (1976), pp. 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Written Opinion of the International Searching Authority for PCT/US08/71825, Oct. 31, 2008.
Written Opinion for the International Searching Authority for PCT/US08/80321, Mar. 17, 2009.
International Preliminary Report on Patentability for PCT/US2008/075282, Mar. 18, 2010.
Written Opinion of the International Searching Authority for PCT/US08/75282, Apr. 22, 2009.
Buslepp, et al. T Cell Activity Correlates with Oligomeric Peptide-Major Histocompatibility Complex Binding on T Cell Surface, JBC, vol. 276, No. 50, pp. 47320-47328, 2001.
Higa et al. Sialogogic activity in rat of peptides analogous to Tyr-sub P in which subst have been made in the N-term amino acids, Archives of Oral Biology, 2001, 46: 313-321.
Kirsch et al. Isolation of recombinant BMP receptor IA ectodomain and its 2:1 complex with BMP-2, FEBS Letters, 2000, 468: 215-219.
Loftus et al. Differential Contact of Disparate Class I/Peptide Complexes as a Basis for Epitope Cross-Recognition by T Cell Receptor, J. Immunology, 1997, 158: 3651-3658. Feb. 1, 2011, Second Exam Report for Canadian Patent Appn No. 2569864.
Jan. 12, 2011, European Search Report for EP Appn No. 10177135.0.
Jun. 23, 2010, European Search Report for EP Appn No. 09173344.4.
Aug. 8, 2010, European Search Report for EP Appn No. 115219.EP.01.

* cited by examiner

*Primary Examiner* — Marcela M Cordero Garcia
(74) *Attorney, Agent, or Firm* — Laura L. Kiefer

(57) ABSTRACT

The presently disclosed subject matter relates to a peptide composition for non-covalently localizing fibrous connective tissue-inducing growth factor to a surface of an implant, the composition comprising a peptide having binding affinity for a surface material of an implant coupled to a peptide having binding affinity for a fibrous connective tissue-inducing growth factor. Methods are provided for delivering fibrous connective tissue-inducing growth factor GDF-7 in an amount effective to promote fibrous connective tissue repair and fibrous connective tissue formation. Also provided are methods of applying the peptide composition to an implant by contacting the composition with a surface of the implant; and kits comprising the compositions.

13 Claims, 2 Drawing Sheets

METHODS AND COMPOSITIONS FOR DELIVERY OF GROWTH FACTOR TO FIBROUS CONNECTIVE TISSUE

CROSS REFERENCE TO RELATED APPLICATIONS

The presently disclosed subject matter claims the benefit of U.S. Provisional Patent Application Ser. No. 60/969,748 filed Sep. 4, 2007; the disclosure of which is incorporated herein by reference in its entirety.

GRANT STATEMENT

The invention was made from government support under Grant No. 1R43AR053753-01 awarded by the National Institute of Arthritis and Musculoskeletal and Skin Diseases. The U.S. Government has certain rights in the invention.

FIELD

The presently disclosed subject matter relates to compositions for delivery of growth factor to fibrous connective tissues. More particularly, the presently disclosed subject matter is directed to a family of peptides having binding affinity to growth factors which are critical for fibrous tissue regeneration, such peptides being useful in compositions and methods related to implants for one or more of repairing defects of fibrous connective tissue, or inducing fibrous connective tissue formation.

BACKGROUND

Annually in the U.S., of the nearly 5 million individuals who visit a physician for tendon pain, approximately 200,000 individuals elect to have a surgical repair. Injuries to tendons and ligaments are quite common, and the frequency of these injuries is expected to rise as the population ages and continues to remain active. Tendon repair surgeries are especially common in the U.S., including rotator cuff tendons (51,000 per year), the Achilles tendon (44,000 per year), and the patella tendon (42,000 per year).

Long periods of immobilization and rehabilitation are required because healing of fibrous connective tissue, such as tendons and ligaments, is a time consuming process. Immobilization of injured fibrous connective tissue allows for the healing process to initiate, while minimizing movement which could disrupt the healing process and/or re-injure the healing fibrous connective tissue. However, as soon as the healing process provides enough mechanical strength in, and integrity of, the healing fibrous connective tissue, the individual is generally encouraged to "rehabilitate" the tissue. Rehabilitation of healing fibrous connective tissue is generally accomplished by promoting an active range of motion, which is believed to promote better return of tissue function, accelerate tissue healing, and improve quality of the tissue repair. Further, a decrease in the immobilization period of a limb or joint is desired, as even a period of 6-8 weeks of immobilization can lead to muscle atrophy, joint stiffness, tendon adhesions, risk of osteoarthritis, and other complications. Thus, any treatment that can shorten this time period by improving the rate of healing (and, hence the strength of the repaired tissue), will also improve care by allowing the individual to resume activity sooner.

Although current surgical procedures for repair of injured fibrous connective tissue are generally fairly successful, complications including failure of the repair are not uncommon. For example, chronic degenerative rotator cuff tears present a significant challenge to orthopedic surgeons. Due to tissue loss and retraction, the rotator cuff tears can generate excessive tension following primary repair, and cause failure of the primary repair. Primary repairs of large chronic tears can fail up to 38% of the time because of tendon degeneration and muscle atrophy.

Growth and differentiation factors (GDFs) are members of the family of growth factors belonging to the family of bone morphogenetic proteins (BMPs). GDF-5, GDF-6, and GDF-7 (also known as BMP-14, BMP-13, and BMP-12, respectively) are clearly involved in fibrous connective tissue development and healing, as they stimulate production of fibrous connective tissue in vitro and in vivo. For example, GDF-5 knockout mice have shown this growth factor is essential for normal tendon development. GDF-5 deficiency has also been shown to alter the ultrastructure, mechanical properties, and composition of the Achilles tendon, and significantly delay its healing in an injury model. These GDF proteins are closely related to each other, with amino acid homologies of at least between 80 to 86%. Additionally, the amino acid identity between rodent and human GDFs is 97% for GDF5, 99% for GDF6, and 97% for GDF-7.

In vivo experiments of tendon repair have raised concerns regarding dosage of GDF. GDFs are capable of driving the differentiation of a range of cell types, including osteblasts and chondrocytes, in addition to tenocytes. Therefore, application of GDFs in a dosage other than a proper dose range to a tendon repair site, or application of GDF outside a tendon repair site, runs the risk of inducing the formation of unwanted bone and/or cartilage. Islands of cartilage have been seen in preclinical animal models investigating GDF-7, especially at the higher doses used. Thus, while growth factors often exert potent therapeutic activity on tissue, they can also trigger ectopic or unwanted responses from healthy or untargeted tissue. Of particular concern, growth factors such as GDFs, and particularly at high or unextended dosages, are capable of driving ectopic differentiation of joints, tendon, cartilage and bone. Therefore, delivery of these growth factors must employ a minimal effective dosage of growth factor which is tightly restricted to a particular region. Although few techniques have been explored for delivering growth factors (e.g., polymers eluting growth factor) and to satisfy these delivery demands, there remains a lack of success.

Thus, there remains a need for a system for localized delivery and retention of growth factors to a site of fibrous connective tissue to be treated for promoting healing and/or growth of fibrous connective tissues.

SUMMARY

The presently disclosed subject matter relates to peptide compositions for delivery of fibrous connective tissue-inducing growth factor to the surface of an implant to promote fibrous connective tissue formation and repair. Also provided in the presently disclosed subject matter are implants coated with the peptide compositions and methods for delivery of fibrous connective tissue-inducing growth factor to the surface of an implant. The peptide compositions comprise a surface binding peptide having binding affinity for a polymer surface material of an implant coupled to a peptide having binding affinity for a fibrous connective tissue-inducing growth factor. Kits comprising the peptide compositions are also provided.

BRIEF DESCRIPTION OF THE DRAWINGS

In FIG. 1, fibrous connective tissue-inducing growth factor GDF-7 is shown bound to the peptide.

In FIG. 2, the peptide used having binding affinity for a surface material of an implant was either SEQ ID NO: 67 (white boxes) or SEQ ID NO: 71 (light gray boxes). Similarly, the peptide used having binding affinity for binding affinity for fibrous connective tissue-inducing growth factor was SEQ ID NO: 2 (dark grey boxes). In addition, the peptides in FIG. 2 comprise one or more of fatty acid terminal modifications or fatty acid linkers (light jagged cloud is undecanoic acid and dark jagged cloud is myristic acid), PEG linkers (MP is mini-PEG and P10 is PEG 10) and amino acid linkers (GSSG).

DETAILED DESCRIPTION

Figure 1:
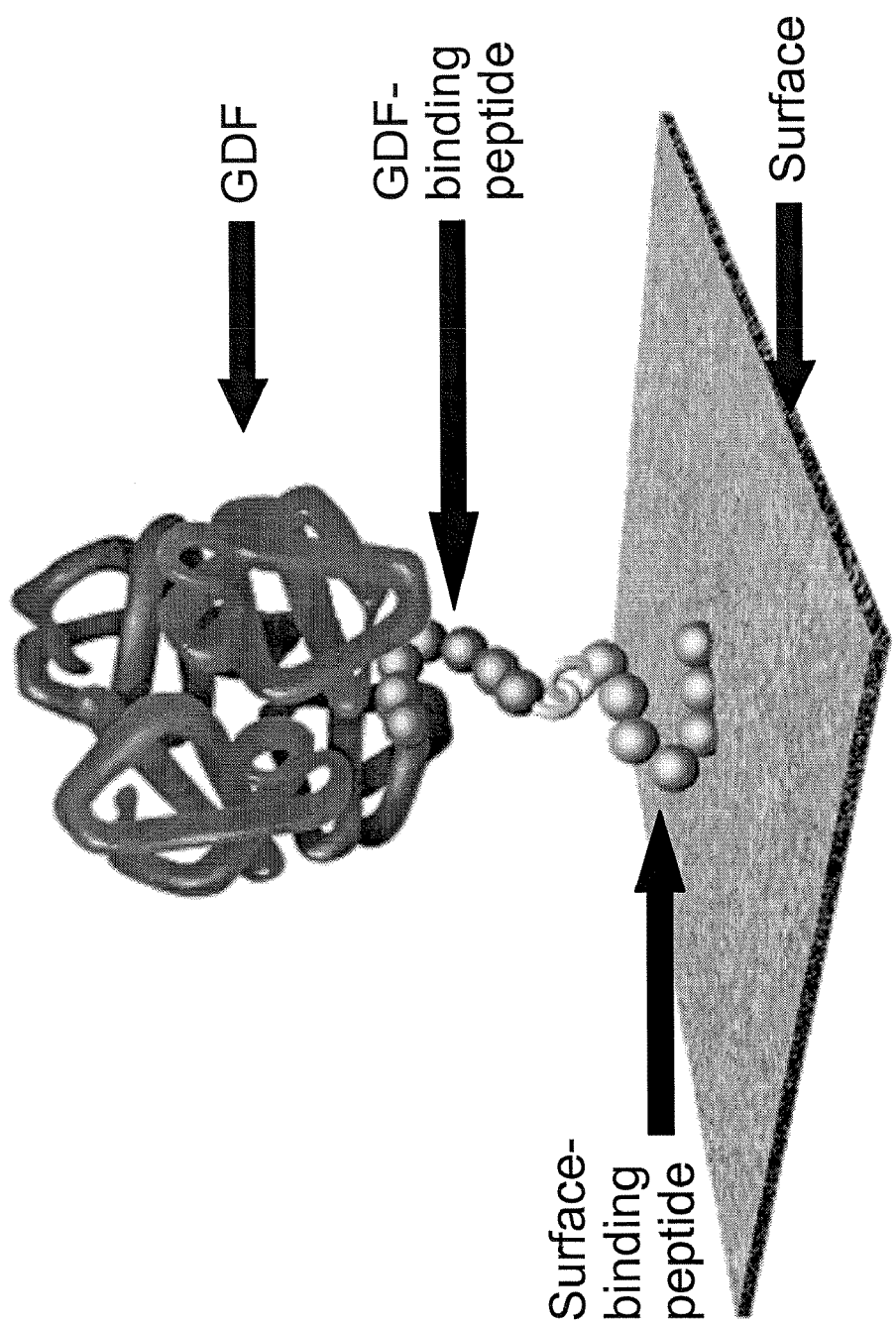
FIG. 1 is a schematic diagram showing a peptide of the presently disclosed subject matter that has binding affinity for a surface material of an implant coupled to a peptide that has binding affinity for fibrous connective tissue-inducing growth factor.

Primary healing of most soft tissues, including basic cell proliferation and vascularization, requires 7 to 10 days. However, because large quantities of collagen must be synthesized and adequately remodeled to form fibrous connective tissue with sufficiently integrity to withstand the forces generated during the wide range of movements of limbs (muscle to bone for tendons; bone to bone for ligaments), healing of fibrous connective tissue can take several weeks. For example, tendon healing can occur intrinsically, by proliferation of epitenon and endotenon tenocytes; or can occur extrinsically, by invasion of cells from the surrounding sheath and synovium. Intrinsic repair relies solely on the tissue's own cells to effect healing. Extrinsic repair relies on cellular infiltration from external tissue sources. Both modes are involved in fibrous connective tissue repair, with extrinsic repair being involved early in the process, and with intrinsic repair being involved later in the process. Extrinsic repair can cause adhesions, as surrounding tissues incorporate into the scar tissue. Adhesions can result in impaired range of motion of the fibrous connective tissue newly formed.

In one embodiment of the presently disclosed subject matter, compositions are provided for delivering fibrous connective tissue-inducing growth factor to a surface of an implant, and for stimulating production of fibrous connective tissue. The fibrous connective tissue-inducing growth factor, as delivered by the composition on a surface of an implant in situ, can stimulate production of fibrous connective tissue in vivo. Thus, the composition can be useful in promoting one or more of repair of fibrous connective tissue or formation of fibrous connective tissue at the site of the implant. A composition according to the presently disclosed subject matter has binding affinity for fibrous connective tissue-inducing growth factor, and can comprise fibrous connective tissue-inducing growth factor bound thereto. Thus, for example, using a composition according to the presently disclosed subject matter to coat a material used to suture damaged tendon edges together retains and delivers fibrous connective tissue-inducing growth factor directly at the site of repair, and can help promote repair of fibrous connective tissue (preferably intrinsic repair) by extended release of fibrous connective tissue-inducing growth factor from the coated suture material. Release of such growth factor from the suture material can locally stimulate migration and proliferation of tenocytes directly at the sutured site (e.g., at an area where repair of fibrous connective tissue is needed). In contrast, direct injections of a bolus of growth factors at a site of tendon repair, without a targeting molecule, can be more likely to diffuse into surrounding tissues and stimulate extrinsic repair and ectopic tissue formation.

Accordingly, the presently disclosed subject matter relates to compositions comprising peptide having binding affinity for growth factors capable of inducing formation of fibrous connective tissue ("fibrous connective tissue-inducing growth factor"), such as one or more of growth factors GDF-5, GDF-6, and GDF-7 (BMP-14, BMP-13, and BMP-12, respectively). In one embodiment, the peptide shows preferential binding to GDF-7 (BMP-12), as compared to any member of the family of GDF, BMP, or TGF-β (transforming growth factor beta) superfamily, other than GDF-7. In one embodiment, the composition comprises a coating composition comprised of peptide according to the presently disclosed subject matter bound specifically to fibrous connective tissue-inducing growth factor. In one example of this embodiment, the coating composition can be contacted with an implant, wherein the peptide component (e.g., peptide having binding affinity for fibrous connective tissue-inducing growth factor) of the composition couples to a surface (e.g., the material of which the surface is comprised), or a portion thereof of the implant, in forming a coating on the surface or portion thereof of the implant. In another example of this embodiment, the coating composition comprises at least one peptide having binding affinity for the surface of an implant (such surface preferably comprising a polymer) coupled to at least one peptide having binding affinity for fibrous connective tissue-inducing growth factor, and can further comprise fibrous connective tissue-inducing growth factor bound to the at least one peptide having binding affinity for fibrous connective tissue-inducing growth factor. In this latter example, the coating composition is applied to (e.g., contacted with) a surface of an implant desired to be coated such that binding specifically to such surface is the component of the composition comprising peptide having binding affinity for the surface, in forming a coating on the surface of the implant.

In another aspect of this presently disclosed subject matter, provided is a family of peptides that share structure and function, in that the peptides comprise amino acid sequence having shared sequence features, and have binding affinity for fibrous connective tissue-inducing growth factor. Related to this aspect of this presently disclosed subject matter, provided are nucleotide sequences and vectors encoding such peptides. Accordingly, in one embodiment, the presently disclosed subject matter provides a peptide composition for extended release of fibrous connective tissue-inducing growth factor from the composition, such release primarily involving dissociation of fibrous connective tissue-inducing growth factor from a peptide to which it is bound via the binding affinity of the peptide.

The peptide composition of the presently disclosed subject matter can comprise a therapeutically effective amount of a single member of fibrous connective tissue-inducing growth factor (e.g., GDF-5), or can comprise a therapeutically effective amount of more than one member of fibrous connective tissue-inducing growth factor (e.g., GDF-5 and GDF-7; or any combination of GDFs). As a combination of more than one member of GDF protein family, each member can be present as a monomer or multimer, and can also be present as heteromers (e.g., comprising a dimer comprised of a monomer of one GDF family member (e.g., GDF-5), and a monomer of a different GDF family member (e.g., GDF-6)). As will be described in more detail herein, various peptides useful in producing the composition according to the presently disclosed subject matter can vary in their ability to bind specifically and preferentially to one or more GDF proteins (see Examples 1 & 2 herein). The choice of whether to include a single member of the GDF protein family or to include more than one member of the GDF protein family, in the composition according to the presently disclosed subject matter will depend on the desired therapeutic response and the indication to be treated.

The presently disclosed subject matter also provides a method of delivering fibrous connective tissue-inducing growth factor to a surface, or portion thereof, of an implant to which is desired to be localized one or more fibrous connective tissue-inducing growth factors. The method comprises applying to the surface a peptide composition according to the presently disclosed subject matter comprising a peptide having binding affinity for fibrous connective tissue-inducing growth factor and fibrous connective tissue-inducing growth factor, wherein the peptide and fibrous connective tissue-inducing growth factor are noncovalently coupled. In one embodiment, the delivery of fibrous connective tissue-inducing growth factor to a surface of an implant is prior to implantation (e.g., at the point of manufacture, or at the point of care). The application of the composition to the implant can be in a form wherein the composition is already pre-formed (e.g., all of the components of the composition are pre-assembled in forming the composition prior to applying the composition to the implant); or the application of the composition to the implant can be in steps wherein the composition is formed on the implant surface (e.g., first coupling to a surface of an implant, a component comprising a peptide having binding affinity for fibrous connective tissue-inducing growth factor, and then in a subsequent step, applying fibrous connective tissue-inducing growth factor to the implant surface having already coupled thereto a peptide having binding affinity for fibrous connective tissue-inducing growth factor, in forming a composition according to the presently disclosed subject matter).

In another embodiment, a composition according to the presently disclosed subject matter can be applied to an implant already implanted into or onto an individual (e.g., applied to the implant "in situ"). In an example of this embodiment, the composition can be applied to the implant in situ such as by administration by injection to the site of an implanted implant; or in the case of an open site, such as by spraying or otherwise suitably applying the composition to the implant. The composition contacts a surface of the implant and couples to the implant in forming a coating on the implant. Preferably, the composition is administered in an amount effective for the desired therapeutic response for the indication (injury, defect, condition, etc.) involving fibrous connective tissue at the site of the implant. For example, such a composition can comprise at least one peptide having binding affinity for the surface of an implant coupled to at least one peptide having binding affinity for fibrous connective tissue-inducing growth factor, and can further comprise fibrous connective tissue-inducing growth factor bound to the at least one peptide having binding affinity for fibrous connective tissue-inducing growth factor.

DEFINITIONS

While the following terms are believed to be well understood by one of ordinary skill in the art, the following definitions are set forth to facilitate explanation of the presently disclosed subject matter.

The term "fibrous connective tissue" is used herein for purposes of the specification and claims, and as known to those skilled in the art, to mean fibrocollagenous tissue comprising a substantial portion of collagen for flexibility and tensile strength; wherein representative examples of fibrous connective tissue include tendon, ligament, dermis of the skin, and sclera of the eye.

The term "fibrous connective tissue-inducing growth factor" is used herein for purposes of the specification and claims, and as known to those skilled in the art, to mean growth factor capable of inducing formation of fibrous connective tissue, such growth factor including but not limited to, for example, GDF-5, GDF-6, GDF-7 (BMP-14, BMP-13, and BMP-12, respectively; "GDF" is an acronym for growth and differentiation factor), BMP-2 ("BMP" is an acronym for bone morphogenetic protein, and BMP-6 (included because it can stimulate ligament fibroblasts which participate in tissue repair). In a preferred embodiment, the peptide shows preferential binding to GDF-7 (BMP-12), as compared to any member of the GDF family, BMP family, or TGF-β (transforming growth factor beta) superfamily, other than GDF-7.

The terms "first" and "second" are used herein for purposes of the specification and claims for ease of explanation in differentiating between two different molecules, and are not intended to be limiting the scope of the presently disclosed subject matter, nor imply a spatial, sequential, or hierarchical order unless otherwise specifically stated.

The term "implant", as used herein for purposes of the specification and claims and in context of fibrous connective tissue, refers to a substance or structure (a) that can be positioned into or onto an individual's body to prevent, treat, modulate or ameliorate damage or a disorder or disease or condition, repair or restore a function of a damaged fibrous connective tissue, or to provide a new function relative to an area of fibrous connective tissue; and (b) comprises at least one surface to which is to be applied a composition according to the presently disclosed subject matter. For example, an implant can be used to promote one or more of fibrous connective tissue healing and repair, treating fibrous connective tissue inflammation (e.g., tendonitis), treating defects of fibrous connective tissue, and inducing formation of fibrous connective tissue in an individual in need thereof. Representative implants include, but are not limited to, sutures (e.g., used for fibrous connective tissue injuries), a matrix used to support and/or provide a surface for fibrous connective tissue formation (which can include, but are not limited to, a biodegradable sponge, surgical mesh, a tendon wrap (e.g., "wrap" meaning a matrix wrapped around the desired fibrous connective tissue; also sometimes referred to in the art as a "sleeve"), a ligament wrap, a prosthesis for fibrous connective tissue, collagen scaffolds, collagen threads, composite collagen felts (see, e.g., U.S. Pat. No. 7,252,832)), a ligament augmentation device, a synthetic graft (e.g. a synthetic ligament graft, tendon replacement, and the like), and a scleral buckle. The material of which a surface of an implant is comprised can comprise a polymer, and the polymer can comprise a synthetic polymer. For example, representative sutures, synthetic ligament grafts, ligament prostheses, and ligament augmentation devices are typically comprised of polymer (e.g., one or more of polyethylene terephthalate, polytetrafluorethylene, polyester, and poly-lactide poly-glycolide co-polymers), and typically in a form comprising braids, fibers, or meshes.

The term "polymer"" is used herein for purposes of the specification and claims to mean a molecule or material comprised of repeating structural units (a structural unit typically referred to as a monomer) connected by covalent chemical bonds. Depending on its intended use, a polymer can be biodegradable (e.g., one or more of self-dissolving, or bioresorbable, or degradable in vivo) or non-biodegradable; or synthetic (manufactured, and not found in nature) or natural (found in nature, as made in living tissues of plants and/or animals).

Non-limiting examples of suitable synthetic polymers described as being biodegradable include: poly-amino acids; polyanhydrides including maleic anhydride polymers; polycarboxylic acid; some polyethylenes including, but not limited to, polyethylene glycol, polyethylene oxide; polypropylenes, including, but not limited to, polypropylene glycol, polypropylene fumarate; one or more of polylactic acid or polyglycolic acid (and copolymers and mixtures thereof, e.g., poly(L-lactic acid) (PLLA), poly(D,L-lactide), poly(lactic acid-co-glycolic acid), 50/50 (DL-lactide-co-glycolide)); polyorthoesters; polydioxanone; polyphosphazenes; polydepsipeptides; one or more of polycaprolactone (and co-polymers and mixtures thereof, e.g., poly(D,L-lactide-co-caprolactone) or polycaprolactone co-butylacrylate; polyhydroxybutyrate valerate and blends; some polycarbonates (e.g., tyrosine-derived polycarbonates and arylates), polyiminocarbonates, calcium phosphates; cyanoacrylate; some polyamides (including nylon); polyurethane; polydimethyltrimethylcarbonates; synthetic cellulosic polymers (e.g, cellulose acetate, cellulose butyrate, cellophane); and mixtures, combinations, and copolymers of any of the foregoing. Representative natural polymers described as being biodegradable include macromolecules (such as polysaccharides, e.g., alginate, starch, chitosan, cellulose, or their derivatives (e.g., hydroxypropylmethyl cellulose); proteins and polypeptides, e.g., gelatin, collagen, albumin, fibrin, fibrinogen); polyglycosaminoglycans (e.g. hyaluronic acid, chondroitin sulfate); and mixtures, combinations, composites (e.g., composite collagen-polymer substrates), and copolymers of any of the foregoing.

Non-limiting examples of suitable synthetic polymers described as being non-biodegradable include: inert polyaryletherketones, including polyetheretherketone ("PEEK"), polyether ketone, polyetherketoneketone, and polyetherketoneetherketoneketone; polyurethanes; polystyrene, and styrene-ethylene/butylene-styrene block copolymers; polyisobutylene copolymers and styrene-isobutylene-styrene block copolymers; polyvinylpyrrolidone; polyvinyl alcohols; copolymers of vinyl monomers; polyvinyl ethers; polyvinyl aromatics; polyethylene oxides; polyesters including polyethylene terephthalate; some polyamides; polyacrylamides; polyethers including polyether sulfone; polyalkylenes including polypropylene, polyethylene; copolymers of ethylene and polypropylene; some polycarbonates, silicone and silicone rubber; siloxane polymers; polytetrafluoroethylene; expanded polytetrafluoroethylene (e-PTFE); nylons and related polyamide copolymers; nylon; fluorinated ethylene propylene; hexafluororopropylene, polymethylmethacrylate (PMMA); 2-hydroxyethyl methacrylate (PHEMA); polyimides; polyethyleneterephthalate; polysulfone, and polysulfides; and mixtures, combinations, and copolymers (including cross-linked copolymers) of any of the foregoing.

The phrase "binding affinity" is used, for the purposes of the specification and claims, to refer to the ability of a peptide (as described herein) to have a binding affinity that is greater for one target molecule or surface material over another; e.g., an affinity for a given molecule in a heterogeneous population of molecules. For example, a peptide has binding affinity for fibrous connective tissue-inducing growth factor when the peptide demonstrates preferential binding to fibrous connective tissue-inducing growth factor, as compared to binding to another biological component or growth factor (e.g., platelet-derived growth factor). As another example, a peptide has binding affinity for a surface comprising a polymer when the peptide demonstrates preferential binding to polymer, as compared to binding to another surface material such as a metal. Such preferential binding can be dependent upon the presence of a particular conformation, structure, and/or charge on or within the peptide and/or material for which it has binding affinity. In some embodiments, a peptide that has binding affinity for a polymeric surface or a fibrous connective tissue-inducing growth factor binds with at least 10% greater affinity, or 20%, 30%, 40%, 50%, 60%, 70%, 80%, 90%, 100%, 200%, 300%, 400% or 500% greater affinity, or a higher percentage, than the peptide binds to, for example, a different non-polymeric surface or a non-fibrous connective tissue-inducing growth factor. For example, binding affinity can determined by an assay in which a signal is quantified (e.g., fluorescence, or calorimetric) representing the relative amount of binding between a peptide and fibrous connective tissue-inducing growth factor. In a preferred embodiment, a peptide has a binding affinity that is characterized by a relative binding affinity as measured by an EC50 of 10 µM or less, and more preferably less than 1 µM and more preferably less than 100 nM. The EC50 can be determined using any number of methods known in the art, such as by generating a concentration response curve from a binding assay in which the concentration of the peptide is titered with a known amount of the substrate for which the peptide has binding affinity. In such case, the EC50 represents the concentration of peptide producing 50% of the maximal binding observed for that peptide in the assay.

The term "peptide" when referring to a peptide of the presently disclosed subject matter is used herein, for the purposes of the specification and claims, to refer to an amino acid chain comprising at least one binding domain and having no less than about 10 amino acids and no more than about 100 amino acid residues in length, wherein the amino acid chain can include naturally occurring amino acids, synthetic amino acids, genetically encoded amino acids, non-genetically encoded amino acids, and combinations thereof; however, an antibody is specifically excluded from the scope and definition of a peptide having a binding domain of the presently disclosed subject matter. In another embodiment, the peptide of the presently disclosed subject matter comprising at least one binding domain can have no less than about 11 amino acids and no more than about 60 amino acid residues in length, or no less than about 12 amino acids and no more than about 40 or 50 amino acid residues in length. The peptide binding domain according to the presently disclosed subject matter comprises a contiguous sequence of no less than about 10 amino acids and no more than about 30 amino acids in length, and more preferably comprises 11, 12, 13, 14, 15, 16, 17, 18, 19, 20, 21, 22, 23, 24 or 25 amino acids in length. The peptide binding domains of the presently disclosed subject matter include surface-binding domains and fibrous connective tissue-inducing growth factor binding domains. The term peptide according to the presently disclosed subject matter includes any pharmaceutical acceptable salt or ester thereof. A peptide used in accordance with the presently disclosed subject matter can be produced by chemical synthesis, recombinant expression, biochemical or enzymatic fragmentation of a larger molecule, chemical cleavage of larger molecule, a combination of the foregoing or, in general, made by any other method in the art, and preferably isolated. The term "isolated" means that the peptide is substantially free of components which have not become part of the integral structure of the peptide itself; e.g., such as substantially free of cellular material or culture medium when produced by recombinant techniques, or substantially free of chemical precursors or other chemicals when chemically synthesized or produced using biochemical or chemical processes.

Peptides can include L-form amino acids, D-form amino acids, or a combination thereof. Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; ornithine; and 3-(3,4-dihydroxyphenyl)-L-alanine ("DOPA"). Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

Further, a peptide according to the presently disclosed subject matter can be modified, such as by addition of chemical moieties, or substitutions, insertions, and deletions of amino acids, where such modifications provide for certain advantages in its use. Thus, the term "peptide" encompasses any of a variety of forms of peptide derivatives including, for example, amides, conjugates with proteins, cyclic peptides, polymerized peptides, conservatively substituted variants, analogs, fragments, chemically modified peptides, and peptide mimetics. Any peptide derivative that has desired binding characteristics of the family of peptides according to the presently disclosed subject matter can be used in the practice of the presently disclosed subject matter. For example, a chemical group, added to the N-terminal amino acid of a synthetic peptide to block chemical reactivity of the amino terminus of the peptide, comprises an N-terminal group. Such N-terminal groups for protecting the amino terminus of a peptide are well known in the art, and include, but are not limited to, lower alkanoyl groups, acyl groups, sulfonyl groups, and carbamate forming groups. Preferred N-terminal groups can include acetyl, Fmoc, and Boc. A chemical group, added to the C-terminal amino acid of a synthetic peptide to block chemical reactivity of the carboxy terminus of the peptide, comprises a C-terminal group. Such C-terminal groups for protecting the carboxy terminus of a peptide are well known in the art, and include, but are not limited to, an ester or amide group. Terminal modifications of a peptide are often useful to reduce susceptibility by proteinase digestion, and to therefore prolong a half-life of peptides in the presence of biological fluids where proteases can be present. Terminal modifications of a peptide can also include fatty acids modifications. Optionally, a peptide, as described herein, can comprise one or more amino acids that have been modified to contain one or more chemical groups (e.g., reactive functionalities such as fluorine, bromine, or iodine) to facilitate linking the peptide to a linker molecule. As used herein, the term "peptide" also encompasses a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO—), and a thiopeptide bond (CS—NH).

Peptides that are useful in a composition according to the presently disclosed subject matter also include peptides having one or more substitutions, additions and/or deletions of residues relative to the sequence of an exemplary peptide disclosed in Tables 1 & 3 and SEQ ID NOs:1-71 and 73-76 herein, so long as the binding properties of the original exemplary peptides are substantially retained. Thus, the presently disclosed subject matter includes peptides that differ from the exemplary sequences disclosed herein by about 1, 2, 3, 4, 5, 6, 7, or 8 amino acids (depending on the length of the exemplary peptide disclosed herein), and that share sequence identity with the exemplary sequences disclosed herein of at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater sequence identity. Sequence identity can be calculated manually or it can be calculated using a computer implementation of a mathematical algorithm, for example, GAP, BESTFIT, BLAST, FASTA, and TFASTA, or other programs or methods known in the art. Alignments using these programs can be performed using the default parameters. A peptide having an amino acid sequence consisting essentially of a sequence of an exemplary peptide disclosed herein can have one or more different amino acid residues as a result of substituting an amino acid residue in the sequence of the exemplary peptide with a functionally similar amino acid residue (a "conservative substitution"); provided that peptide containing a conservative substitution will substantially retain the binding affinity of the exemplary peptide not containing the conservative substitution. Examples of conservative substitutions include the substitution of one non-polar (hydrophobic) residue such as isoleucine, valine, leucine or methionine for another; the substitution of one aromatic residue such as tryptophan, tyrosine, or phenylalanine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue such as aspartic acid or glutamic acid for another.

In another embodiment, the peptides of the presently disclosed subject matter include the exemplary peptides disclosed in Tables 1 & 3, and SEQ ID NOs:1-71 and 73-76 that can comprise additional amino acids at the carboxyl and/or amino terminal ends (e.g., ranging from 1 to up to about 40 additional amino acids at one or both ends) so long as the binding properties of the original exemplary peptides are substantially retained. For example, the peptides comprising additional amino acids at one or both ends retain binding affinity to one or both of the fibrous connective tissue-inducing growth factor or the surface-binding affinity as described herein. For example, peptides comprising additional amino acids at one or both ends of the exemplary amino acid sequences illustrated as SEQ ID NOs: 1-71 and 73-76 will possess binding affinity for fibrous connective tissue-inducing growth factor and/or surface-binding affinity as provided herein, and will not possess any characteristics which constitutes a significant change in binding affinity (e.g., a significant change comprising greater than about a 10 to about a 100 to about a 1000 fold or more difference in binding affinity).

The term "pharmaceutically acceptable carrier", when used herein for purposes of the specification and claims, means a carrier medium that is a suitable support medium for administration and/or application of a composition according to the presently disclosed subject matter, and preferably does not significantly alter the biological activity of the composition according to the presently disclosed subject matter to which it is added. Examples of such a carrier medium include, but are not limited to, aqueous solutions, aqueous or non-aqueous solvents, suspensions, emulsions, gels, pastes, and the like. As known to those skilled in the art, a suitable pharmaceutically acceptable carrier can comprise one or substances, including but not limited to, water, buffered water, medical parenteral vehicles, saline, 0.3% glycine, aqueous alcohols, isotonic aqueous buffer; and can further include one or more substances such as water-soluble polymer, glycerol, polyethylene glycol, glycerin, oils, salts such as sodium, potassium, magnesium and ammonium, phosphonates, carbonate esters, fatty acids, saccharides, polysaccharides, glycoproteins (for enhanced stability), excipients, and preservatives and/or stabilizers (to increase shelf-life or as necessary and suitable for manufacture and distribution of the composition).

The term "linker" is used, for purposes of the specification and claims, to refer to a compound or moiety that acts as a molecular bridge to covalently couple at least two different molecules (e.g., with respect to the presently disclosed subject matter, coupling at least one peptide having binding affinity for fibrous connective tissue-inducing growth factor to a surface of an implant, or to a peptide having binding affinity for a surface material of an implant). Thus, for example, one portion (e.g., a "first" reactive functionality) of the linker binds to at least one peptide having binding affinity for polymer, and another portion (e.g., a "second" reactive functionality) of the linker binds to at least one peptide having binding affinity for a fibrous connective tissue-inducing growth factor. As known to those skilled in the art, and using methods known in the art, two molecules can be coupled to the linker in a step-wise manner, or can be coupled simultaneously to the linker. There is no particular size or content limitations for the linker so long as it can fulfill its purpose as a molecular bridge, and that the binding affinity of the peptide in a composition according to the presently disclosed subject matter is substantially retained.

Linkers are known to those skilled in the art to include, but are not limited to, chemical chains, chemical compounds (e.g., reagents), and the like. The linkers can include, but are not limited to, homobifunctional linkers and heterobifunctional linkers. Heterobifunctional linkers, well known to those skilled in the art, contain one end having a first reactive functionality (chemical group or chemical moiety) to specifically link a first molecule, and an opposite end having a second reactive functionality to specifically link to a second molecule. It will be evident to those skilled in the art that a variety of bifunctional or polyfunctional reagents, both homo- and hetero-functional (such as those described in the catalog of the Pierce Chemical Co., Rockford, Ill.), amino acid linkers (typically, a short peptide of between 3 and 15 amino acids, and often containing amino acids such as glycine, and/or serine), and polymers (e.g., polyethylene glycol) can be employed as a linker with respect to the presently disclosed subject matter. In one embodiment, representative peptide linkers comprise multiple reactive sites to be coupled to a binding domain (e.g., polylysines, polyornithines, polycysteines, polyglutamic acid and polyaspartic acid) or comprise substantially inert peptide linkers (e.g., lipolyglycine, polyserine, polyproline, polyalanine, and other oligopeptides comprising alanyl, serinyl, prolinyl, and/or glycinyl amino acid residues). Linkers can also utilize copper-catalyzed azide-alkyne cycloaddition (e.g., "click chemistry") or any other methods well known in the art. Linkers are known in the art and include linkers that can be cleaved (e.g., by heat, by natural enzymes found in or on the body of an individual, by pH sensitivity), and linkers that can be made reactive toward other molecular moieties or toward themselves, for cross-linking purposes. Examples of pH-sensitive materials useful as linkers can include, but are not limited to, cellulose acetate phthalate, cellulose acetate trimellitate, polyvinyl acetate phthalate, hydroxypropyl methylcellulose phthalate, and hydroxypropyl methylcellulose acetate succinate. Depending on such factors as the molecules to be linked, and the conditions in which the linking is performed, the linker can vary in length and composition for optimizing such properties as preservation of biological function, stability, resistance to certain chemical and/or temperature parameters, and of sufficient stereo-selectivity or size. For example, the linker should not significantly interfere with the ability of a composition to sufficiently bind to a surface, with appropriate avidity for the purpose, or to bind to fibrous connective tissue-inducing growth factor. A preferred linker can be a molecule having activities that enhance or complement the function of the composition of the presently disclosed subject matter.

Suitable polymeric linkers are known in the art, and can comprise a synthetic polymer or a natural polymer. Representative synthetic polymers include but are not limited to polyethers (e.g., poly(ethylene glycol) ("PEG"), 10 unit poly (ethylene glycol) ("P10"), mini-PEG which is Fmoc-8-Amino-3,6-Dioxaoctanoic Acid ("MP")), polyesters (e.g., polylactic acid (PLA) and polyglycolic acid (PGA)), polyamines, polyamides (e.g., nylon), polyurethanes, polymethacrylates (e.g., polymethylmethacrylate; PMMA), polyacrylic acids, polystyrenes, polyhexanoic acid, flexible chelators such as EDTA, EGTA, and other synthetic polymers which preferably have a molecular weight of about 20 daltons to about 1,000 kilodaltons. Representative natural polymers include but are not limited to hyaluronic acid, alginate, chondroitin sulfate, fibrinogen, fibronectin, albumin, collagen, calmodulin, and other natural polymers which preferably have a molecular weight of about 200 daltons to about 20,000 kilodaltons (for constituent monomers). Polymeric linkers can comprise a diblock polymer, a multi-block copolymer, a comb polymer, a star polymer, a dendritic or branched polymer, a hybrid linear-dendritic polymer, a branched chain comprised of lysine, or a random copolymer. A linker can also comprise a mercapto(amido)carboxylic acid, an acrylamidocarboxylic acid, an acrlyamido-amidotriethylene glycolic acid, 7-aminobenzoic acid, and derivatives thereof.

In another embodiment, the linkers of the presently disclosed subject matter can be fatty acids. The fatty acids of the presently disclosed subject matter include saturated and unsaturated fatty acids such as but not limited to butyric acid, caproic acid, caprylic acid, capric acid, undecanoic acid (AUD), lauric acid, myristic acid, palmitic acid, stearic acid, arachidic acid, behenic acid, lignoceric acid, eicosanoic acid, docosanoic acid, tetracosanoic acid, myristoleic acid, palmitoleic acid, oleic acid, linoleic acid, α-linolenic acid, arachidonic acid, eicosapentaenoic acid, erucic acid, and docosahexaenoic acid. For example, in some embodiments, the fatty acid linkers are used as a linking group between the surface-binding peptide and the fibrous connective tissue-inducing growth factor binding peptide. In addition to their use as linkers, the fatty acid molecules of the presently disclosed subject matter can be used in other embodiments to modify the surface-binding peptide and the fibrous connective tissue-inducing growth factor binding peptide. For example, in some embodiments fatty acids are used to modify the amino- and/or the carboxyl-terminal end of the peptide compositions comprising a surface-binding peptide and a fibrous connective tissue-inducing growth factor binding peptide.

The term "effective amount" is used herein, in relation to a composition according to the presently disclosed subject matter and a substrate comprising an implant to which it binds or is coupled, and for purposes of the specification and claims, to mean an amount sufficient of the composition so as to mediate binding of the composition to the substrate; in promoting attachment of the composition to a substrate. The term "effective amount" is used herein, in referring to use of a composition according to the presently disclosed subject matter for one or more of repairing defects of fibrous connective tissue or inducing fibrous connective tissue formation, and for purposes of the specification and claims, to mean an amount of fibrous connective tissue-inducing growth factor in the composition effective for modulating, preventing, ameliorating, or treating the condition and/or disease comprising fibrous connective tissue intended to be treated.

The term "peptide composition" is used herein, in reference to the presently disclosed subject matter and for purposes of the specification and claims, to refer to a peptide composition comprising peptide having binding affinity for fibrous connective tissue-inducing growth factor coupled to a peptide having binding affinity for a polymer substrate of which an implant is comprised. The coupling of the peptide having binding affinity for fibrous connective tissue-inducing growth factor to the peptide having binding affinity for a polymer substrate can occur in either orientation. For example, the peptide having binding affinity for fibrous connective tissue-inducing growth factor can occur at either the amino- or the carboxyl-terminus of the peptide composition. The peptide having binding affinity for a polymer substrate can similarly occur at either terminus. The peptide composition can further comprise bound fibrous connective tissue-inducing growth factor and one or more of a linker coupled to the peptide according to the presently disclosed subject matter, one or more amino- and/or carboxyl-terminal modifications according to the presently disclosed subject matter, a pharmaceutically acceptable carrier, and a combination thereof. Thus, a peptide composition of the presently disclosed subject matter can be represented by formula I: SBP-L-GDFBP or GDFBP-L-SBP, wherein SBP is a peptide of 10 to 100 amino acids comprising (i) a surface-binding domain of 10 to 30 amino acids and (ii) binding affinity for a polymer surface material of an implant; GDFBP is a peptide of 10 to 100 amino acids comprising (i) a fibrous connective tissue-inducing growth factor-binding domain of 10 to 30 amino acids and (ii) binding affinity for a fibrous connective tissue-inducing growth factor; and L can be present or absent and comprises a covalent linker between SBP and GDFBP, wherein if L is absent SBP and GDFBP are linked directly together.

SBP can be coupled to GDFBP in such a way that each retains its respective binding affinity. Such coupling can include forming a multimeric molecule having two or more peptides having binding affinity for a surface of an implant, two or more peptides having binding affinity for fibrous connective tissue-inducing growth factor, and a combination thereof. For example, using standard reagents and methods known in the art of peptide chemistry, two peptides can be coupled via a side chain-to-side chain bond (e.g., where each of the peptides has a side chain amine (e.g., such as the epsilon amine of lysine)), a side chain-to-N terminal bond (e.g., coupling the N-terminal amine of one peptide with the side chain amine of the other peptide), a side chain-to-C-terminal bond (e.g., coupling the C-terminal chemical moiety (e.g., carboxyl) of one peptide with the side chain amine of the other peptide), an N-terminal-to-N-terminal bond, an N-terminal to C-terminal bond, a C-terminal to C-terminal bond, or a combination thereof. In synthetic or recombinant expression, a peptide having binding affinity for a surface of an implant can be coupled directly to a peptide having binding affinity for fibrous connective tissue-inducing growth factor by synthesizing or expressing both peptides as a single peptide. The coupling of two or more peptides can also be via a linker.
[End of Formal Definition Section]

The presently disclosed subject matter provides for a family of peptides having binding affinity for fibrous connective tissue-inducing growth factor; peptide compositions comprising a peptide according to the presently disclosed subject matter; methods for coating an implant by applying to the implant a peptide composition according to the presently disclosed subject matter; and a coated implant wherein the coating comprises a peptide composition according to the presently disclosed subject matter; all of these aspects of the presently disclosed subject matter relating to peptides having binding affinity for fibrous connective tissue-inducing growth factor. Exemplary peptides having binding affinity for fibrous connective tissue-inducing growth factor comprise a peptide selected from the group consisting of an amino acid selected from the group consisting of SEQ ID NOs:1-11, 73, 74, or 75, a peptide having 95% identity with any one or more of SEQ ID NOs: 1-11, 73, 74, or 75, a conservatively substituted variant thereof, a modified peptide thereof (i.e., the peptide being modified to comprise one or more of a terminal modification, and a modification to facilitate linking), and a combination thereof.

The following examples are provided to further describe certain aspects of the presently disclosed subject matter and are not intended to limit the scope of the presently disclosed subject matter.

EXAMPLE 1

Illustrated in this example are various methods for utilizing phage display technology to produce a peptide having binding affinity for fibrous connective tissue-inducing growth factor according to the presently disclosed subject matter. Many of the peptides comprising the binding domains in a coating composition according to the presently disclosed subject matter (i.e., a peptide having binding affinity for a surface of an implant, and a peptide having binding affinity for fibrous connective tissue-inducing growth factor) were initially developed using phage display technology, followed by peptide design and peptide synthesis to result in improved binding properties.

Phage Screening and Selections

Phage display technology is well-known in the art, and can be used to try to identify phage-displayed peptides having binding affinity for a certain target substrate used in screening. In general, using phage display, a library of diverse peptides can be presented to a target substrate, and peptides that specifically bind to the substrate can be selected for use as binding domains. Multiple serial rounds of selection, called "panning," can be used. As is known in the art, any one of a variety of libraries and panning methods can be employed in practicing phage display technology. Panning methods can include, for example, solution phase screening, solid phase screening, or cell-based screening. Once a candidate binding domain is identified, directed or random mutagenesis of the sequence can be used to optimize the binding properties (including one or more of affinity and avidity) of the binding domain.

For example, a variety of different phage display libraries were screened for peptides that bind to a selected target substrate (e.g., a substrate selected to find a binding domain useful in the presently disclosed subject matter). The substrate was either bound to or placed in (depending on the selected substrate) a container (e.g., wells of a 96 well microtiter plate, or a microfuge tube). Nonspecific binding sites on the surfaces of the container were blocked with a buffer containing bovine serum albumin ("BSA"; e.g., in a range of from 1% to 10%). The containers were then washed 5 times with a buffer containing buffered saline with Tween™ 20 ("buffer-T"). Each library was diluted in buffer-T and added at a concentration of $10^{10}$ pfu/ml in a total volume of 100 µl. After incubation (in a range of from 1 to 3 hours) at room temperature with shaking at 50 rpm, unbound phage were removed by multiple washes with buffer-T. Bound phage were then used to infect E. coli cells in growth media. The cell and phage-containing media was cultured by incubation overnight at 37° C. in a shaker at 200 rpm. Phage-containing supernatant was harvested from the culture after centrifuging the culture. Second and third rounds of selection were performed in a similar manner to that of the first round of selection, using the amplified phage from the previous round as input. To detect phage that specifically bind to the selected substrate, enzyme-linked immunosorbent (ELISA-type) assays were performed using an anti-phage antibody conjugated to a detector molecule, followed by the detection and quantification of the amount of detector molecule bound in the assay. The DNA sequences encoding peptides from the phage that specifically bind to the selected substrate were then determined; i.e., the sequence encoding the peptide is located as an insert in the phage genome, and can be sequenced to yield the corresponding amino acid sequence displayed on the phage surface.

As a specific illustrative example, GDF-7 was used as a substrate for performing phage selection using several different libraries of phage. GDF-7 was immobilized for phage selections using two different methods. In a first method, GDF-7 (4 pmol/well, in a volume of 100 µl/well) in a buffer of 0.1 M $NaCO_3$ was used to pre-coat wells of a microtiter plate. In a second method, a buffered solution of anti-GDF antibody (1 µg/ml a volume of 100 µl/well) was used to pre-coat wells of a microtiter plate, followed by the addition of GDF-7 (4 pmol/well) to the antibody pre-coated wells of a microtiter plate. Pre-coating typically involved an overnight incubation at 4° C., followed by several washes with buffer-T. Nonspecific binding sites in the well surfaces of the microtiter plate were blocked with 1% bovine serum albumin (BSA) in 0.1 M $NaHCO_3$. The plate was incubated for 1 hour at room temperature with shaking at 50 rpm. The wells were then washed 5 times with 300 µl of buffer-T.

Each library was diluted in high salt (0.5 M NaCl) buffer-T with 1% BSA, and added to each well of the microtiter plates at a concentration of $10^{10}$ pfu/ml in a total volume of 100 µl. After 2 hours of incubation at room temperature and shaking at 50 rpm, unbound phage were removed by 5 washes of buffer-T. The phage were added to E. coli cells susceptible to phage infection in 2×YT media, and the phage-infected cells were transferred to a fresh tube containing 2×YT media and incubated overnight at 37° C. in a shaker incubator. Phage supernatant was harvested by centrifugation at 8500×g for 10 minutes. Second and third rounds of selection were performed in a similar manner to the first round, using the amplified phage from the previous round as input. Each round of selection was monitored for enrichment of GDF-7-binding peptides using ELISA-like assays, and by phage titer. Libraries that showed enrichment of phage displaying peptides binding to GDF-7 were plated on a lawn of E. coli cells, and individual plaques were picked and tested for binding to fibrous connective tissue-inducing growth factors by the ELISA assay. For the ELISA, using the methods described herein, GDF-7 was immobilized directly, or via an absorbed antibody, on the well surfaces of a microtiter plate. Phage was added to the wells (25 µl of the phage dilution) along with 75 µl high-salt buffer-T with 1% BSA, followed by incubation at room temperature for 1 hour. Following several washes with buffer-T, added was anti-M13 phage antibody conjugated to horseradish-peroxidase, followed by the addition of chromogenic agent ABTS (2,2'-azino-bis(3-ethylbenzthiazoline-6-sulphonic acid), and determining a read-out at 405 nm at 20 minutes. The resultant absorbance value for each well correlates to the amount of phage bound to GDF-7.

Primers against the phage vector sequence that flank the insertion site were used to determine the DNA sequence encoding the peptide for the phage in each group. The sequence encoding the peptide insert was translated to yield the corresponding amino acid sequence displayed on the phage surface. The DNA sequences encoding peptides isolated using GDF-7 were determined and are shown in Table 1. While typically such phage amino acids adjoining the peptide displayed had no significant contribution to the binding affinity of the peptide, the peptides according to the presently disclosed subject matter can also comprise, in their amino acid sequence, such phage amino acids adjoining the peptide at the N-terminus and at the C-terminus (e.g., denoted as ss and sr in Table 1).

TABLE 1

Peptide sequences isolated by phage selections using GDF-7

| SEQ ID NO: 1 | Amino acid sequence |
|---|---|
| 1 | ssGPREIWDSLVGVVNPGWsr |
| 2 | ssGGVGGWALFETLRGKEVsr |
| 3 | ssVAEWALRSWEGMRVGEAsr |
| 4 | ssWEETGWRDFNSLRGREVsr |
| 5 | SREAHVGWGVFEALQGVTVsr |
| 6 | ssVGWDEFMSLRGVEKKGWsr |
| 7 | ssPSWDQFQSLVGVPTWAAsr |
| 8 | ssGLLGGWSGLQGVELWSSsr |

From an alignment of amino acid sequences of peptides identified by phage selections on immobilized GDF-7, a consensus amino acid sequence (SEQ ID NO:9) was constructed, as follows: SEQ ID NO: 9: $X_1XaaXaaX_2X_3X_4X_5X_6X_7XaaX_8$, wherein Xaa is any amino acid; $X_1$ is W, R or L; $X_2$ is F or W; $X_3$ is E, D, N, M, Q or S; $X_4$ is S, T, G or A; $X_5$ is L or M; $X_6$ is R, Q or V; $X_7$ is G or V; and $X_8$ is E, V, T or P.

SEQ ID NO: 10: $X_1X_2X_3X_4X_5X_6\ X_7X_8X_9X_{10}X_{11}$, wherein $X_1$ is W, R or L; $X_2$ is A, E or R; $X_3$ is L, I or S; $X_4$ is F or W; $X_5$ is E, D, N, M, Q or S; $X_6$ is S, T, G or A; $X_7$ is L or M; $X_8$ is R, Q or V; $X_9$ is G or V; $X_{10}$ is K, R, V or G; and $X_{11}$ is E, V, T or P.

SEQ ID NO: 11: $X_1X_2X_3X_4X_5X_6\ X_7X_8X_9X_{10}X_{11}$, wherein $X_1$ is W, R, or L, and preferably W; $X_2$ is A, E or R; $X_3$ is L, I or S; $X_4$ is F or W; $X_5$ is E or D; $X_6$ is S, T or G; $X_7$ is L or M; $X_8$ is R or V; $X_9$ is G or V; $X_{10}$ is K, V or G; and $X_{11}$ is E or V.

Using the consensus sequence, a consensus peptide can comprise an amino acid sequence consisting essentially of WXXFE(S/T)LXGXEX (SEQ ID NO:12), wherein X is any amino acid.

Thus, provided is an isolated peptide having binding affinity for fibrous connective tissue-inducing growth factor, the peptide comprising a consensus amino acid sequence selected from the group consisting of SEQ ID NO: 9, SEQ ID NO: 10, SEQ ID NO: 11, an amino acid sequence containing up to two amino acids additions, deletions, or replacements to SEQ ID NO: 9, SEQ ID NO: 10 or SEQ ID NO: 11 ("substituted variant" of SEQ ID NO: 9, SEQ ID NO: 10 or SEQ ID NO: 11), and a modified amino acid sequence thereof comprising one or more of a terminal modification, and a modification to facilitate linking of the peptide. Thus, such a peptide can have an amino acid sequence selected from the group consisting of SEQ ID NOs: 1-8, 12, 73, 74, and 75. Preferably, the peptide according to the presently disclosed subject matter has a binding affinity for fibrous connective tissue-inducing growth factor that is represented by a relative binding affinity to GDF-7 of an EC50 of less than 1 μM and more preferably of less than 100 nM. In a preferred embodiment, the substituted variant has at least 90% identity to any one of SEQ ID NO: 9, SEQ ID NO: 10 or SEQ ID NO: 11.

EXAMPLE 2

In this example, illustrated are further characterizations of peptides according to the presently disclosed subject matter. Peptides according to the presently disclosed subject matter can be synthesized using any method known to those skilled in the art including, but not limited to, solid phase synthesis, solution phase synthesis, linear synthesis, and a combination thereof. In this example, peptides were synthesized using standard solid-phase peptide synthesis techniques on a peptide synthesizer using standard Fmoc chemistry. After all residues were coupled, simultaneous cleavage and side chain deprotection was achieved by treatment with a trifluoroacetic acid (TFA) cocktail. Crude peptide was precipitated with cold diethyl ether and purified by high performance liquid chromatography (HPLC) using a linear gradient of water/acetonitrile containing 0.1% TFA. Homogeneity of the synthetic peptides was evaluated by analytical reverse phase-HPLC, and the identity of the peptides was confirmed with mass spectrometry.

Binding Affinity Characterizations

Relative binding affinities of representative peptides of the presently disclosed subject matter to fibrous connective tissue-inducing growth factor were determined by testing serial dilutions of the peptide for binding to fibrous connective tissue-inducing growth factor. Plotting the absorbance observed across the concentration range for each peptide sequence yielded a binding curve of the peptides to fibrous connective tissue-inducing growth factor from an EC50 was determined (i.e., the concentration of peptide that gives 50% of the maximum signal in the binding curve). Preferred are peptides that bind to fibrous connective tissue-inducing growth factor with binding affinity, preferably with an EC50 of less than or equal to about 1 μM, and more preferably, in the nanomolar range (e.g., <100 nM). Thus, in a preferred embodiment, in the methods and compositions according to the presently disclosed subject matter, a preferred peptide demonstrates binding affinity for fibrous connective tissue-inducing growth factor with an EC50 of less than or equal to about 1 μM, and more preferably, <100 nM. A typical binding assay for fibrous connective tissue-inducing growth factor can be performed according to the following procedure.

Briefly, peptides comprising an amino acid sequence of each of SEQ ID NOs: 1-3 were biotinylated to facilitate immobilization on streptavidin-coated 96-well plates. The microtiter plates were coated with streptavidin by adding 50 μl of a 10 μg/ml streptavidin solution in 0.1 M NaHCO$_3$, and incubating the plates for at least 3 hours. The plate wells were blocked by adding 150 μl of a 1% BSA solution in 0.1 M NaHCO$_3$, and the plates were stored at 4° C. until needed. Before use, the streptavidin plates were washed extensively in buffer-T. Peptides were then added at 20 pmol per well in 100 μl of high-salt buffer-T (containing 500 mM NaCl), and then incubated for 1 hour at room temperature with shaking. 150 μl of 0.5 mM biotin in H$_2$O was added to block the remaining streptavidin sites, and plates were incubated for an additional hour. Plates were then washed with TBS-T to remove the excess biotin and peptide. Serial dilutions of growth factor (including fibrous connective tissue-inducing growth factors GDF-7, GDF-5, BMP-2, and BMP-6,; and growth factors other than fibrous connective tissue-inducing growth factors, such as BMP-5, TGF-β, TGF-β3, or PDGF-BB) in high-salt buffer-T were added (100 μl) to each well, representing a range of concentrations between 0.01 nM and 100 nM. Plates were incubated for 1 hour at room temperature with shaking prior to washing several times with TBS-T. Growth factors were then detected using 100 μl of the appropriate dilutions of primary antibodies specific for the growth factor being detected. After washing with buffer-T, 100 μl of alkaline phosphatase-conjugated secondary antibody was added to each well and incubated at room temperature for 45 minutes. Excess secondary antibody was removed by repeated washes with buffer-T, and the amount of alkaline phosphatase remaining in the well was detected using a pNPP (para-nitrophenylphos-phate) colorimetric enzymatic assay. The amount of growth factor captured by the peptides was determined by measuring the absorbance at 405 nm of the colored product of the alkaline phosphatase reaction. The EC50 was determined for each peptide relative to the binding affinity for the various growth factors, as shown in Table 2.

TABLE 2

| Growth factor | SEQ ID NO: 1 EC50 | SEQ ID NO: 2 EC50 | SEQ ID NO: 3 EC50 |
|---|---|---|---|
| GDF-7 | <1 nM | <1 nM | <1 nM |
| GDF-5 | <10 nM | <10 nM | <10 nM |
| BMP-2 | <10 nM | <10 nM | <10 nM |
| BMP-6 | <10 nM | <10 nM | <10 nM |
| BMP-5 | <100 nM | <100 nM | <100 nM |
| TGF-β1 | ndb | ndb | ndb |
| TGF-β3 | ndb | ndb | ndb |
| PDGF-BB | ndb | ndb | ndb | ndb—no detectable binding (e.g., relative to negative control and assay background).

Since GDFs are also considered as members of the BMP family of proteins, and therefore share significant amino acid sequence homology, some binding cross-reactivity of peptides according to the presently disclosed subject matter with BMP-5 was noted. However, all the growth factors listed in Table 2 are in the TGF-β superfamily, and thus share sequence homology; yet the peptides of the presently disclosed subject matter demonstrate binding affinity primarily for fibrous connective tissue-inducing growth factors rather than for other members of the TGF-β superfamily outside of the BMP/GDF families of growth factor. Further binding studies were performed from which was determined the preference of binding of peptides according to the presently disclosed subject matter for various growth factors. For peptides having an amino acid sequence of either of SEQ ID NOs: 1 or 3, the preference for binding affinity (from highest relative binding affinity to lowest) as follows: GDF-7>GDF-5, BMP-2>BMP-6>BMP-5>TGF-β1, TGF-β3, or PDGF-BB (the latter 3 showing no detectable binding to the peptides). For a peptide having an amino acid sequence of SEQ ID NO: 2, the preference for binding affinity is as follows: GDF-7>GDF-5, BMP-2, and BMP-6>BMP-5>TGF-β1, TGF-β3, or PDGF-BB (the peptide showing no detectable binding to the latter 3 growth factors, but significantly more binding to GDF-7 than to any of BMP-2, BMP-6 and GDF-5, as compared to SEQ ID NO: 1 or SEQ ID NO: 3). Thus peptides according to the presently disclosed subject matter show preferential binding to GDF-7, and show binding affinity for fibrous connective tissue-inducing growth factors.

A competition assay was performed to determine if peptides having the amino acid sequences of SEQ ID NOs: 1, 2, and 3 bound to GDF-7 at similar or overlapping sites. A binding assay was performed as described above with an immobilized peptide being one of SEQ ID NOs: 1, 2, or 3; but in addition to adding GDF-7, added to the reaction solution was a competitor peptide (any one of SEQ ID NOs: 1, 2, or 3) in increasing concentration up to a 1000-fold molar excess of the immobilized peptide. If the competitor peptide binds to GDF-7 at a similar site on GDF-7 with high affinity as compared to the immobilized peptide, then a relatively low concentration of competitor peptide would be needed to inhibit GDF-7 binding to the immobilized peptide. From these studies, peptides having amino acid sequences of SEQ ID NOs: 1, 2, and 3 appear to have a similar binding site on GDF-7.

EXAMPLE 3

Table 3 illustrates exemplary peptides having binding affinity for a surface material of an implant ("surface-binding peptides"). For example, surface-binding peptides include amino peptides comprising surface binding domains and having binding affinity for materials including but not limited to, for example, polystyrene, polyurethane, polyglycolic acid, polycarbonate, nylon, Teflon®, polyethylene terephthalate fibers and collagen-based substrates. Exemplary surface-binding peptides include SEQ ID NOs: 13-71. In some embodiments, at least one surface-binding peptide can be coupled to at least one peptide having binding affinity for fibrous connective tissue-inducing growth factor in producing a composition according to the presently disclosed subject matter.

TABLE 3

| SEQ ID NO: | Binding affinity for polystyrene Amino acid sequence (single letter code) |
|---|---|
| 13 | FLSFVFPASAWGG |
| 14 | FYMPFGPTWWQHV |
| 15 | LFSWFLPTDNYPV |
| 16 | FMDIWSPWHLLGT |
| 17 | FSSLFFPHWPAQL |
| 18 | SCAMAQWFCDRAEPHHVIS |
| 19 | SCNMSHLTGVSLCDSLATS |
| 20 | SCVYSFIDGSGCNSHSLGS |
| 21 | SCSGFHLLCESRSMQRELS |

TABLE 3-continued

| 22 | SCGILCSAFPFNNHQVGAS |
| 23 | SCCSMFFKNVSYVGASNPS |
| 24 | SCPIWKYCDDYSRSGSIFS |
| 25 | SCLFNSMKCLVLILCFVS |
| 26 | SCYVNGHNSVWVVVFWGVS |
| 27 | SCDFVCNVLFNVNHGSNMS |
| 28 | SCLNKFFVLMSVGLRSYTS |
| 29 | SCCNHNSTSVKDVQFPTLS |
| 30 | FFPSSWYSHLGVL |
| 31 | FFGFDVYDMSNAL |
| 32 | LSFSDFYFSEGSE |
| 33 | FSYSVSYAHPEGL |
| 34 | LPHLIQYRVLLVS |

| SEQ ID NO: | Binding affinity for polyurethane Amino acid sequence (single letter code) |
|---|---|
| 35 | SCYVNGHNSVWVVVFWGVS |

| SEQ ID NO: | Binding affinity of polyglycolic acid (Amino acid sequence single letter code) |
|---|---|
| 36 | SCNSFMFINGSFKETGGCS |
| 37 | SCFGNLGNLIYTCDRLMPS |
| 38 | SCSFFMPWCNFLNGEMAVS |
| 39 | SCFGNVFCVYNQFAAGLFS |
| 40 | SCCFINSNFSVMNHSLFKS |
| 41 | SCDYFSFLECFSNGWSGAS |
| 42 | SCWMGLFECPDAWLHDWDS |
| 43 | SCFWYSWLCSASSSDALIS |
| 44 | SCFGNFLSFGFNCESALGS |
| 45 | SCLYCHLNNQFLSWVSGNS |
| 46 | SCFGFSDCLSWFVQPSTAS |
| 47 | SCNHLGFFSSFCDRLVENS |
| 48 | SCGYFCSFYNYLDIGTASS |
| 49 | SCNSSSYSWYCWFGGSSPS |

| SEQ ID NO: | Binding affinity for polycarbonate Amino acid sequence (single letter code) |
|---|---|
| 50 | FGHGWLNTLNLGW |
| 51 | FSPFSANLWYDMF |
| 52 | VFVPFGNWLSTSV |
| 53 | FWNVNYNPWGWNY |

TABLE 3-continued

| | |
|---|---|
| 54 | FYWDRLNVGWGLL |
| 55 | LYSTMYPGMSWLV |

| SEQ ID NO: | Binding affinity for nylon<br>Amino acid sequence (single letter code) |
|---|---|
| 56 | SCFYQNVISSSFAGNPWEC |
| 57 | SCNMLLNSLPLPSEDWSAC |
| 58 | SCPFTHSLALNTDRASPGC |
| 59 | SCFESDFPNVRHHVLKQSC |
| 60 | SCVFDSKHFSPTHSPHDVC |
| 61 | SCGDHMTDKNMPNSGISGC |
| 62 | SCDFFNRHGYNSGCEHSVC |
| 63 | SCGDHMTDKNMPNSGISGC |
| 64 | SCYYNGLVVHHSNSGHKDC |

| SEQ ID NO: | Binding affinity for Teflon<br>Amino acid sequence (single letter code) |
|---|---|
| 66 | CWSRFRLFMLFCMFYLVS |
| 66 | CIKYPFLYCCLLSLFLFS |

| SEQ ID NO: | Binding affinity for polyethylene terephthalate fibers |
|---|---|
| 67 | SWWGFWNGSAAPVWSR |
| 68 | SWDFRSLRDWWPPAPSLSSR |

| | Binding affinity for collagen-based substrates |
|---|---|
| 69 | SIFSTWNPWSPYSVSR |
| 70 | SFGSWWWGSGAASSR |

| | Designed peptide |
|---|---|
| 71 | YFRAFRKFVKPFKRAFK |

EXAMPLE 4

This example illustrates a method of making a composition according to the presently disclosed subject matter comprising coupling together at least one peptide having binding affinity for a surface material of an implant with at least one peptide having binding affinity for fibrous connective tissue-inducing growth factor. Using methods described herein and methods well known in the art for coupling (directly or via use of a linker) together two molecules, for example, a peptide having binding affinity for a surface of an implant can be coupled to a peptide having binding affinity for fibrous connective tissue-inducing growth factor, in forming a composition according to the presently disclosed subject matter useful for coating an implant. As apparent to one skilled in the art, a method of preference for coupling or linking two molecules will vary according to the reactive functionalities present on each molecule. As known to those skilled in the art, a reactive functionality which can be used in covalently coupling can comprise a chemical group selected from the group consisting of a maleimide, thiol, carboxy, hydrogen, phosphoryl, acyl, hydroxyl, acetyl, aldehyde, hydrophobic, amine, amido, dansyl, sulfhydryl, a succinimide (including but not limited to a succinimidyl ester or succinimidyl carbonate), a halogen, a thiol-reactive chemical group, an amine-reactive chemical group, a carboxyl-reactive chemical group, a hydroxyl-reactive chemical group, and a combination thereof.

To illustrate this embodiment, a linker was used to couple a peptide having binding affinity for a surface of an implant with a peptide having binding affinity for fibrous connective tissue-inducing growth factor. Since many commercially available sutures are comprised of braided polyethylene terephthalate fibers, and peptide comprising amino acid sequence SEQ ID NO: 67 showed binding affinity for this suture material (e.g., surface material of an implant), this peptide was chosen as a representative surface-binding peptide for inclusion as a component in a composition according to the presently disclosed subject matter. Similarly, peptides having amino acid sequences of SEQ ID NOs: 1-3 were used individually as representative peptides having binding affinity for fibrous connective tissue-inducing growth factor, and for inclusion as a component in a composition according to the presently disclosed subject matter.

Using standard methods for peptide synthesis, amino acid sequences comprising SEQ ID NO:1-3 and SEQ ID NO: 67 were synthesized to contain an amino acid linker sequence (e.g., GSSGK, SEQ ID NO:72) at the C-terminus to which was linked biotin (via the lysine residue). See, for example, SEQ ID NOs: 73-76. Streptavidin (having 4 biotin binding sites) was used in conjunction with the biotin on the biotinylated peptides to form a linker between the two different peptide components. While various molar ratios were used successfully, in one illustrative example, a 2:1 molar ratio of surface-binding peptide to a peptide having binding affinity for fibrous connective tissue-inducing growth factor was used in the coupling reaction. Thus, 1416 pmol of surface-binding peptide was mixed with 708 pmol of peptide having binding affinity for fibrous connective tissue-inducing growth factor in 30 μl of $H_2O$. To this mixture was added 30 μl of a 1 mg/ml streptavidin stock solution, and the mixture was incubated at room temperature for 10 minutes. The reaction mixture was then chilled on ice for up to 45 minutes. To block any unoccupied biotin-binding sites on streptavidin, added to the reaction mixture was 0.5 mM biotin in 440 μl of high salt buffer-T. Thus, formed is a composition according to the presently disclosed subject matter comprising at least one surface-binding peptide coupled to at least one peptide having binding affinity for fibrous connective tissue-inducing growth factor.

In this example, a composition according to the presently disclosed subject matter was applied to an implant by contacting the implant with (e.g., soaking the implant in a solution containing the) composition for a sufficient time for binding the composition to the implant. Commercial sutures, comprised of polyethylene terephthalate fibers, were cut into lengths of 0.5 cm and placed into wells of a 96 well plate. The wells were then blocked in high salt buffer-T with 1% BSA for 30 minutes at room temperature. A peptide conjugate, for use as an experimental negative control ("control conjugate"), was prepared by binding biotinylated surface-binding peptide to streptavidin (i.e., does not contain peptide having binding affinity for fibrous connective tissue-inducing growth factor).

Each of the three representative compositions according to the presently disclosed subject matter or the control conjugate were added individually to respective wells containing a suture and containing GDF-7 in various concentrations (starting at 100 nM final concentration for the compositions; 0.5 μM of the conjugate) with high salt buffer-T, and incubated for 1 hour at room temperature. The suture was then washed several times with high salt buffer-T. Detection for GDF-7 localized and retained on the suture (i.e., as a result of the composition binding to the suture, and GDF-7 being bound by the composition) was performed using an anti-GDF-7 antibody-secondary antibody-AP conjugate with detection using a pNPP colorimetric enzymatic assay. The peptide conjugate, as is expected of a negative control, showed no appreciable binding (e.g., relative to background for the assay) for GDF-7. A binding curve for each of the three representative compositions was generated for determination of EC50 values, as a measure of the binding affinity for each representative composition for GDF-7 while the respective composition is bound to the implant (e.g., a suture). From the binding curve, each of the 3 representative compositions (each while immobilized on the surface of an implant) demonstrated a binding affinity for GDF-7 represented by an EC50 of less than 10 nM. Conditions for the binding assay were varied, including the time sufficient for maximal amount of GDF-7 to a composition according to the presently disclosed subject matter immobilized on a surface of an implant. It was determined in these experiments that maximal growth factor binding to the composition occurs within the first several minutes (e.g., within a time period ranging from 5 to 10 minutes), and that no additional GDF-7 appears to be retained to the surface of the implant in a time period of up to 1 hour of contact with the implant. These and other data suggest that in application of a composition according to the presently disclosed subject matter to a surface of an implant, a time sufficient for binding the composition to the implant (and for binding fibrous connective tissue-inducing growth factor to the composition) can comprise minimally several minutes of contacting the implant with the composition (or contacting the composition with fibrous connective tissue-inducing growth factor).

To determine retention of a composition according to the presently disclosed subject matter to the surface of an implant, a method for detecting GDF-7 was employed using standard Western blotting techniques. GDF-7 was bound to a composition according to the presently disclosed subject matter (comprising a surface-binding peptide comprising an amino acid sequence of SEQ ID NO: 67 coupled to a peptide having binding affinity for fibrous connective tissue-inducing growth factor comprising an amino acid sequence of SEQ ID NO: 2), and then the composition was contacted and applied to sutures in microfuge tubes, as previously described herein. The sutures were then incubated in the presence of 100% human plasma for 0, 1, 3, or 6 days. At the appropriate time point, the plasma was removed from the tube, the suture was washed briefly, added was gel electrophoresis sample buffer, and the suture was boiled in the sample buffer to elute any GDF which was bound to the suture via the composition. The samples were electrophoresed by standard gel electrophoresis (SDS-PAGE), and then transferred to a membrane by electroblotting. GDF-7 was detected on the immunoblots using anti-GDF-7 antibody and a conjugate of secondary antibody and alkaline phosphate (AP) with subsequent color development, using standard Western-blotting techniques. Also included in this assay were known GDF amounts (e.g., 100 ng, 50 ng, 25 ng, 12.5 ng) which allowed for a standard curve to be constructed using densitometric analyses of the Western blot. In addition to the foregoing experiment for measuring GDF-7 retention on sutures using the peptide streptavidin conjugates, peptides comprising both a surface-binding peptide (SEQ ID NO: 71) covalently linked to a peptide having binding affinity for fibrous connective tissue-inducing growth factor (SEQ ID NO:2) were synthesized using standard methods for peptide synthesis. The GDF-7 retention experiment was performed similarly for the peptides comprising covalently linked binding domains with only minor alterations.

By this assay, over 50 ng/cm of GDF-7 was retained by the peptide streptavidin conjugates and over 80 ng/cm of GDF-7 was retained by the covalently linked peptide compositions and initially immobilized on the suture incubated. As compared to day 0, by day 3 the streptavidin conjugates released about half of the GDF-7 initially bound to the suture and by day 6 released about two-thirds of the GDF-7 initially bound to the suture. By day 4 the covalent peptide compositions released about two thirds of GDF-7 initially bound to the suture. Thus, by this example, demonstrated is the retention and localization of fibrous connective tissue-inducing growth factor to a surface of an implant, via a composition according to the presently disclosed subject matter, and sustained release of the fibrous connective tissue-inducing growth factor from the composition bound to the implant to which it is localized. Additionally, demonstrated is retention by a composition according to the presently disclosed subject matter of biologically relevant amounts of fibrous connective tissue-inducing growth factor to a surface of an implant (for sutures, a biologically effective concentration of a fibrous connective tissue-inducing growth factor for inducing healing of tendon tissue has been reportedly estimated at about 40 ng/cm). In addition, experiment data indicate that a substantial amount of the composition according to the presently disclosed subject matter (including bound fibrous connective tissue-inducing growth factor) can remain coupled to the surface of a suture, even after passing the suture several times through tendon tissue.

EXAMPLE 5

In this example, methods are further illustrated for applying a composition according to the presently disclosed subject matter to an implant. The methods comprise contacting the composition with the at least one surface of the implant to which the composition is to be applied (e.g., the surface to be coated by the composition) with an amount of the composition effective to promote fibrous connective tissue formation (e.g., by releasing fibrous connective tissue-inducing growth factor at site of the implant). An effective amount of the composition can be determined by a physician considering such factors that include, but are not limited to, the type of fibrous connective tissue-inducing growth factor to be delivered, the condition or indication of the fibrous connective tissue to be treated, repaired, ameliorated, the size of the area of tissue damage, the site of the implant, the type of implant, and the amount of fibrous connective tissue desired to be formed. Using methods known in the art, an effective dosage can also be determined from results of pre-clinical and clinical studies using a composition according to the presently disclosed subject matter. Progress or assessment of formation of fibrous connective tissue induced by a composition according to the presently disclosed subject matter can be monitored by methods known in the art, such as by various imaging techniques (e.g., x-ray, computer-assisted tomography (CAT scan), magnetic resonance imaging (MRI), arthroscopy).

The composition can be applied to the implant, wherein the composition comprises fibrous connective tissue-inducing growth factor already bound to the composition at the time of application to the implant. In another embodiment, the peptide having binding affinity for fibrous connective tissue-inducing growth factor is not yet bound to fibrous connective tissue-inducing growth factor at the time the composition is applied to the implant. With respect to the latter, in a further step of coating, the surface material having composition applied thereon is then contacted with a sufficient amount of fibrous connective tissue-inducing growth factor (in vitro or in vivo) under conditions suitable so that fibrous connective tissue-inducing growth factor binds to the composition bound to the surface of the implant. In one example, a composition according to the presently disclosed subject matter is applied to the implant before positioning the implant in situ.

In another example, a composition according to the presently disclosed subject matter is applied to an implant in situ. For example, if the implant is exposed through an open site in the body (e.g., such as in surgery), a physician can spray or otherwise apply the composition to the implant in situ. In another example wherein the implant is not readily accessible by applications such as a spray coating, a composition according to the presently disclosed subject matter can be administered by injection at the site of the implant such that the composition comes in contact with the implant. To facilitate injection of the composition, the composition further comprises a pharmaceutically acceptable carrier. Conventional processes known in the art can be used to apply a coating composition according to the presently disclosed subject matter to the one or more surfaces of an implant to be coated (in contacting the coating composition with the one or more surfaces). Depending on the nature of the implant to be coated, such processes are known to include, but are not limited to, soaking, mixing, dipping, brushing, spraying, and vapor deposition. For example, a solution or suspension comprising the coating composition can be applied through the spray nozzle of a spraying device, creating droplets that coat the surface of the implant to be coated. The coated implant is allowed to dry, and can then be further processed prior to use (e.g., washed in a solution (e.g., water or isotonic buffer) to remove excess coating composition; if for in vivo use, by sterilization using any one or methods known in the art for sterilizing polymer; etc.). Alternatively, the coating composition and the implant can each be sterilized prior to the process of coating, and the application process performed under sterile conditions.

In another process for applying the coating composition to one or more surfaces of an implant to be coated, the surface of the implant to be coated is dipped into a liquid (e.g., solution or suspension, aqueous or solvent) containing coating composition in an amount effective to coat the implant. For example, the surface is dipped or immersed into a bath containing the coating composition. Suitable conditions for applying the coating composition include allowing the surface to be coated to remain in contact with the liquid containing the coating composition for a suitable period of time (e.g., ranging from about 5 minutes to about 12 hours; more preferably, ranging from 5 minutes to 60 minutes), at a suitable temperature (e.g., ranging from 10° C. to about 50° C.; more preferably, ranging from room temperature to 37° C.). The coated implant can then be further processed, as necessary for use (e.g., washing, sterilization, and the like). These illustrative processes for applying a coating composition to an implant are not exclusive, as other coating and stabilization methods can be employed (as one of skill in the art will be able to select the compositions and methods used to fit the needs of the particular implant and purpose).

Additionally, in a method according to the presently disclosed subject matter, a coat on an implant surface comprising the coating composition can be stabilized, for example, by air drying. However, these treatments are not exclusive, and other coating and stabilization methods can be employed. Suitable coating and stabilization methods are known in the art. For example, the at least one surface of the implant to be coated with the coating composition of the presently disclosed subject matter can be pre-treated prior to the coating step so as to enhance one or more of: the binding of peptide having binding affinity for the surface material to be coated; and the consistency and uniformity of the coating.

EXAMPLE 6

In this example, peptide compositions of the presently disclosed subject matter comprising a peptide having binding affinity for a surface material of an implant coupled to a peptide having binding affinity for fibrous connective tissue-inducing growth factor were synthesized comprising one or more of fatty acid terminal modifications, fatty acid linkers, PEG linkers and amino acid linkers. Illustrative peptides of the presently disclosed subject matter and synthesized by the methods described herein are shown in Table 4. The compounds are listed as a linear sequence, with "AUD" representing aminoundecanoic acid, "MYR" representing myristic acid; "Ahx" represents a fatty acid comprising aminohexanoic acid; "B" represents biotin; and "NH2" means a modified C-terminal amino acid that has been amidated. The peptides comprising a peptide having binding affinity for a surface material of an implant coupled to a peptide having binding affinity for fibrous connective tissue-inducing growth factor further include a biotinylated linker at the C-terminal end to facilitate detection during functional studies.

TABLE 4

| Peptide No. | Peptide linear sequence |
|---|---|
| 710P | SEQ ID NO: 2-(AUD)$_6$-SEQ ID NO: 71-GSSGK-B-NH2 |
| 720P | SEQ ID NO: 71-(AUD)$_6$-SEQ ID NO: 2-GSSGK-B-NH2 |
| 730P | (AUD)$_4$-SEQ ID NO: 2-(MP)$_2$-SEQ ID NO: 71-GSSGK-B-NH2 |
| 740P | MYR-Ahx-SEQ ID NO: 2-(MP)$_2$-SEQ ID NO: 71-GSSGK-B-NH2 |
| 750P | SEQ ID NO: 71-(MP)$_2$-SEQ ID NO: 2-GSSGK-B-NH2 |
| 760P | SEQ ID NO: 2-(MP)$_2$-SEQ ID NO: 71-GSSGK-B-NH2 |
| 770P | SEQ ID NO: 2-P10-SEQ ID NO: 71-GSSGK-B-NH2 |
| 780P | SEQ ID NO: 67-GSSG-SEQ ID NO: 2-GSSGK-B-NH2 |
| 790P | SEQ ID NO: 2-GSSG-SEQ ID NO: 67-GSSGK-B-NH2 |
| 800P | SEQ ID NO: 2-(MP)$_2$-SEQ ID NO: 67-GSSGK-B-NH2 |
| 810P | SEQ ID NO: 2-P10-SEQ ID NO: 67-GSSGK-B-NH2 |
| 820P | SEQ ID NO: 2-(AUD)$_6$-SEQ ID NO: 67-GSSGK-B-NH2 |
| 830P | SEQ ID NO: 2-GSSG-SEQ ID NO: 71-GSSGK-B-NH2 |

The following acronyms are used in the description of methods herein for making compounds of the presently disclosed subject matter. Mtt is 4-methyltrityl; TATU is 2-(7-

Aza-1H-Benzotriazole-1-yl)-1,1,3,3-tetramethyluronium tetrafluoroborate; DIEA is diisopropylethylamine; NMP is 1-Methyl-2-pyrrolidone; DCM is dichloromethane; DMF is dimethylformamide; TFA is trifluoroacetic acid; TIS is triisopropylsilane; TBTU is O-(Benzotriazol-1-yl)-N,N,N',N'-tetramethyluronium tetrafluoroborate; HOBt is O-Pfp ester/1-hydroxybenzotriazole; NMM is N-methylmorpholine; RP-HPLC is reverse phase high performance liquid chromatography; Fmoc is 9-fluorenylmethoxycarbonyl; tBU is t-butyl; mini-PEG is Fmoc-8-Amino-3,6-Dioxaoctanoic Acid; MALDI-TOF is matrix-assisted laser desorption ionization-time of flight mass spectrometry; Reagent A is water/TFA (0.1% TFA); Reagent B is Acetonotrile/TFA (0.1% TFA); Fmoc-PAL-PEG resin is [5-(4-Fmoc-aminomethyl-3,5-dimethoxyphenoxy)valeric acid]-polyethylene glycol-polystryrene resin.

Standard Fmoc/t-Bu chemistry using AA/TBTU/HOBt/NMM (1:1:1:2) as the coupling reagents was employed to synthesize exemplary peptide 740P. The base resin, Fmoc-PAL-PEG-PS (~0.20 mmol/g) was used for synthesis of an amino acid sequence comprising SEQ ID NO:71, followed by two mini-PEG linkers, followed by an amino acid sequence comprising SEQ ID NO:2. Amino acids were used in 5 fold excess in the synthesis cycles and all residues were doubly or triply coupled. The coupling reactions were monitored by Kaiser ninhydrin test or chloranil test. In order to suppress peptide aggregation, pseudoproline dipeptides Fmoc-Ser-Ser (PsiMe,Me pro)-OH were employed, and were double coupled in 5 fold excess. Fmoc-Lys(Biotin)-OH and Fmoc-Mini-PEG-$CO_2$H were double coupled manually using the above coupling conditions. Fmoc deprotection reactions were carried out using 20% piperidine in DMF with 0.1 M HOBt. Aminohexanoic acid (Ahx) was introduced at the N-terminus of the resin-bound peptide followed by double coupling of myristic acid using TBTU activation method.

The compound was cleaved from the resin using Reagent K (TFA: EDT:$H_2O$: phenol: thioanisole=82.5:2.5:5:5:5) at room temperature for 4 hours. The crude products were precipitated in cold ether. The pellet obtained after centrifugation was washed thrice with cold ether, and lyophilized to give white solid as crude peptide. The crude linear peptides were cyclized using 3% DMSO in 10 mM PBS (pH 7.4) buffer for 48 hours (peptide concentration~0.065-0.075 mM) The crude cyclic peptide was purified on an RP-HPLC column (C18; 250×21.2 mm) using mobile eluants (A=$H_2O$/TFA (0.1% TFA) and B=Acetonitrile/TFA (0.1% TFA) using a gradient of 15% B to 55% B in 50 min at 10 mL/min @ 220 nm. The fractions containing the desired product were pooled and lyophilized to obtain a fluffy white powder and the desired product was confirmed by MALDI-TOF analysis.

Peptide NOs: 710P-830P were synthesized using similar methods and reagents as described herein for peptide 740P.

EXAMPLE 7

GDF-7 Capture on Sutures

Figure 2:
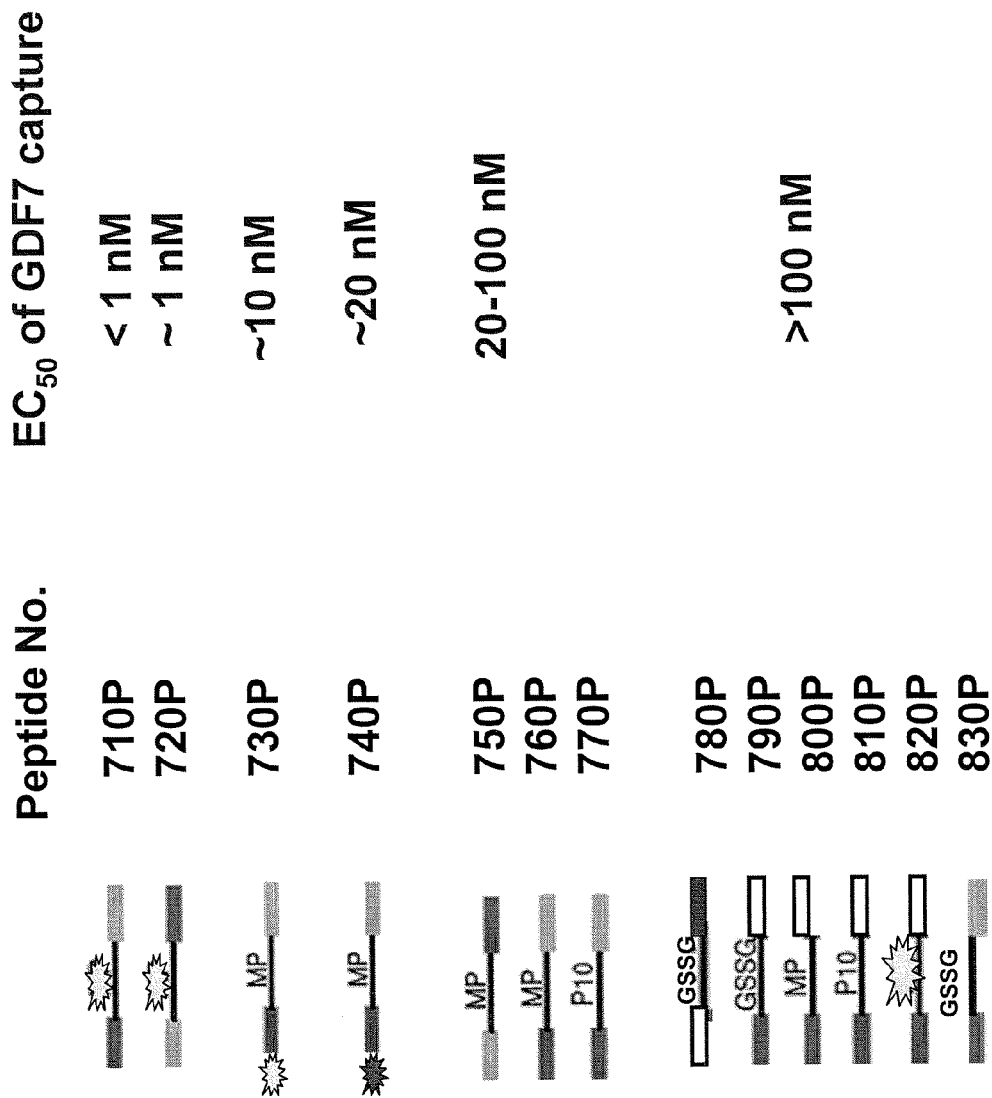
FIG. 2 is a schematic diagram comparing the EC50 values for capture of GDF-7 on sutures for a series of peptides of the presently disclosed subject matter. The peptides comprise a peptide having binding affinity for a surface material of an implant coupled to a peptide having binding affinity for fibrous connective tissue-inducing growth factor.

The following procedure was performed to test the ability of the exemplary peptide compositions of the presently disclosed subject matter comprising a peptide having binding affinity for a surface material of an implant coupled to a peptide having binding affinity for fibrous connective tissue-inducing growth factor to capture GDF-7 on sutures. The peptide compositions described in EXAMPLE 6 (SEQ ID NOS: 710P-830P) were tested as follows. ETHIBOND EXCEL 1 sutures (ETHICON) were cut into 0.5 cm length pieces with razor blade and placed in the wells of a 96-well polypropylene plate. The plate was blocked with 1% BSA/TBS (high salt) for 1 hr at RT by shaking. One µM peptide solutions were prepared in TBST high salt and the peptide solution was added at 100 µl/well/suture. Plates were incubated 30 min at RT shaking. The plates were washed manually with 4×250 µl of TBST high salt. GDF-7 (R&D SYSTEMS) solutions were prepared at a concentration of 50 nM in TBST high salt and added at serial 1:4 dilutions to the sutures in the 96-well plate at a concentration range of 0.01 nM-50 nM. The plate was incubated 1 hr at RT shaking. The plate was washed manually with 4×250 µl of TBST high salt. Detection of GDF-7 was performed using an anti-GDF-7 antibody-secondary antibody-AP conjugate with detection using a pNPP colorimetric enzymatic assay. A relative EC50 value for GDF-7 capture by the peptide compositions was determined. The EC50 values are summarized in FIG. 2.

EXAMPLE 8

It is apparent to one skilled in the art, that based on the amino acid sequence of the peptide comprising an amino acid sequence with binding affinity for fibrous connective tissue-inducing growth factor in accordance with the presently disclosed subject matter, polynucleotides (nucleic acid molecules) encoding such a peptide (or variants thereof as described herein) can be synthesized or constructed, and that such a peptide can be produced by recombinant DNA technology as a means of manufacture (e.g., in culture) and/or in vivo production by introducing such polynucleotides in vivo. For example, it is apparent to one skilled in the art that more than one polynucleotide sequence can encode a peptide according to the presently disclosed subject matter, and that such polynucleotides can be synthesized on the bases of triplet codons known to encode the amino acids of the peptide, third base degeneracy, and selection of triplet codon usage preferred by cell-free expression system or the host cell (typically a prokaryotic cell or eukaryotic cell (e.g., bacterial cells such as E. coli; yeast cells; mammalian cells; avian cells; amphibian cells; plant cells; fish cells; and insect cells; whether located in vitro or in vivo) in which expression is desired. It would be routine for one skilled in the art to generate the degenerate variants described above, for instance, to optimize codon expression for a particular host (e.g., change codons in the bacteria mRNA to those preferred by a mammalian, plant or other bacterial host such as E. coli).

For purposes of illustration only, and not limitation, provided are SEQ ID NOs:77-79 which are polynucleotides encoding amino acid sequences of SEQ ID NOs: 1, 2, and 3, respectively from which, as apparent to one skilled in the art, codon usage will generally apply to polynucleotides encoding a peptide according to the presently disclosed subject matter which has binding affinity for fibrous connective tissue-inducing growth factor. Thus, for example, using SEQ ID NO: 77 in relation to SEQ ID NO: 1, one skilled in the art could readily construct a polynucleotide encoding variants of the amino acid sequence illustrated in SEQ ID NO: 1, or deduce the polynucleotide sequence encoding an amino acid sequence illustrated as SEQ ID NO: 1. In a preferred embodiment of the presently disclosed subject matter, a polynucleotide encoding an amino acid sequence of a peptide having binding affinity for fibrous connective tissue-inducing growth factor comprises a nucleic acid molecule encoding a peptide consisting essentially of the amino acid sequence of the peptide having binding affinity for fibrous connective tissue-inducing growth factor, or an amino acid sequence having at least 95% identity (and more preferably, at least 90% identity) with the amino acid sequence of the peptide having binding affinity for fibrous connective tissue-inducing growth factor, provided the encoded peptide has binding affinity for fibrous connective tissue-inducing growth factor.

In one illustrative embodiment, provided is a recombinant vector comprising a polynucleotide encoding a peptide having binding affinity for fibrous connective tissue-inducing growth factor for use in accordance with the presently disclosed subject matter; and its use for the recombinant production of a peptide having binding affinity for fibrous connective tissue-inducing growth factor. In one example, the polynucleotide can be added to a cell-free expression system known in the art for producing peptides or polypeptides. In another example, the polynucleotide can be positioned in an expression vector so that when the peptide is produced in host cells, it is produced as a fusion protein with other amino acid sequence (e.g., which assist in purification of the peptide; or as recombinantly coupled to a surface-binding domain), or as multiple copies or concatemers of the peptide. For example, there are sequences known to those skilled in the art which, as part of a fusion protein with a peptide desired to be expressed, facilitates production in inclusion bodies found in the cytoplasm of the prokaryotic cell used for expression and/or assists in purification of fusion proteins containing such sequence. Inclusion bodies can be separated from other prokaryotic cellular components by methods known in the art to include denaturing agents, and fractionation (e.g., centrifugation, column chromatography, and the like). In another example, there are commercially available vectors into which is inserted a desired nucleic acid sequence of interest to be expressed as a protein or peptide such that upon expression, purification of the gene product can be accomplished using methods standard in the art.

It is apparent to one skilled in the art that a nucleic acid sequence encoding a peptide having binding affinity for fibrous connective tissue-inducing growth factor according to the presently disclosed subject matter can be inserted into, and become part of a, nucleic acid molecule comprising a plasmid, or vectors other than plasmids; and other expression systems can be used including, but not limited to, bacteria transformed with a bacteriophage vector, or cosmid DNA; yeast containing yeast vectors; fungi containing fungal vectors; insect cell lines infected with virus (e.g. baculovirus); and mammalian cell lines having introduced therein (e.g., transfected or electroporated with) plasmid or viral expression vectors, or infected with recombinant virus (e.g. vaccinia virus, adenovirus, adeno-associated virus, retrovirus, etc.). Successful expression of the peptide requires that either the recombinant nucleic acid molecule comprising the encoding sequence of the peptide, or the vector itself, contain the necessary control elements for transcription and translation which is compatible with, and recognized by the particular host system used for expression.

Using methods known in the art of molecular biology, including methods described above, various promoters and enhancers can be incorporated into the vector or the recombinant nucleic acid molecule comprising the encoding sequence to increase the expression of the peptide, provided that the increased expression of the peptide is compatible with (for example, non-toxic to) the particular host cell system used. As apparent to one skilled in the art, the selection of the promoter will depend on the expression system used. Promoters vary in strength, i.e., ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising $E.\ coli$ include the lac promoter, trp promoter, T7 promoter, recA promoter, ribosomal RNA promoter, the $P_R$ and $P_L$ promoters, lacUV5, ompF, bla, lpp, and the like, can be used to provide transcription of the inserted nucleotide sequence encoding the synthetic peptide. Commonly used mammalian promoters in expression vectors for mammalian expression systems are the promoters from mammalian viral genes. Examples include the SV40 early promoter, mouse mammary tumor virus LTR promoter, adenovirus major late promoter, herpes simplex virus promoter, and the CMV promoter.

In the case where expression of the peptide can be lethal or detrimental to the host cells, the host cell strain/line and expression vectors can be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside ("IPTG"); trp operon is induced when tryptophan is absent in the growth media; and tetracycline can be use in mammalian expression vectors having a tet sensitive promoter). Thus, expression of the peptide can be extended by culturing transformed or transfected cells under conditions such that the promoter controlling the expression from the encoding sequence is not induced, and when the cells reach a suitable density in the growth medium, the promoter can be induced for expression from the encoding sequence. Other control elements for efficient gene transcription or message translation are well known in the art to include enhancers, transcription or translation initiation signals, transcription termination and polyadenylation sequences, and the like.

EXAMPLE 9

In this example, illustrated is a kit comprising a composition according to the presently disclosed subject matter. The components of the kit can include a container containing a composition comprising at least one peptide having binding affinity for a surface material of an implant coupled to at least one peptide having binding affinity for fibrous connective tissue-inducing growth factor. The composition can, optionally, comprise the peptide having binding affinity for fibrous connective tissue-inducing growth factor bound to fibrous connective tissue-inducing growth factor. A preferred type of container is a vial, such as that typically used for solutions or lyophilized powders of medicaments, medicinals, drugs, coatings, and the like.

Alternatively, a component in the kit can be a first container comprising fibrous connective tissue-inducing growth factor, and a second container comprising a composition comprising at least one peptide having binding affinity for a surface material of an implant coupled to at least one peptide having binding affinity for fibrous connective tissue-inducing growth factor. Thus, the fibrous connective tissue-inducing growth factor growth can be added to a composition according to the presently disclosed subject matter in a step of applying the composition to a surface of an implant, rather than as part of a pre-formed composition containing fibrous connective tissue-inducing growth factor growth; or can be mixed with the composition according to the presently disclosed subject matter prior to applying the composition to a surface of an implant. Other components of the kit can include, but are not limited to, a liquid for reconstitution (one or more containers containing a diluent or fluid which can be used to reconstitute a kit component, such as for reconstitution of a composition according to the presently disclosed subject matter and/or fibrous connective tissue-inducing growth factor that can be packaged in lyophilized or powder form); an applicator device for applying the composition to an implant (e.g., a soaking tray, brush, applicator pad, syringe, syringe needle, or combination thereof), instructions for use of the kit, an implant to which is to be applied a composition according to the presently disclosed subject matter, and a combination thereof. A kit comprises such components packaged together, such as in a single sterile container (e.g., box, tray, pouch, or other form of conventional packaging). The kit can also comprise a plurality of individually packaged components, and the individual packages can then be contained within a single larger container. For use in the medical field or dental field, preferably the components will be sterilized within the package or container so that they are immediately ready for use in a sterile environment.

The foregoing description of the specific embodiments of the presently disclosed subject matter have been described in detail for purposes of illustration. In view of the descriptions and illustrations, others skilled in the art can, by applying, current knowledge, readily modify and/or adapt the presently disclosed subject matter for various applications without departing from the basic concept of the presently disclosed subject matter; and thus, such modifications and/or adaptations are intended to be within the meaning and scope of the appended claims.

What is claimed is:

1. A method for stimulating production of fibrous connective tissue in a subject, the method comprising:
   placing an implant comprising a peptide (i) having a sequence at least 95% identical to the sequence set forth in SEQ ID NO: 1 or SEQ ID NO: 3 or (ii) having a sequence with no more than 3 conservative amino acid substitutions in SEQ ID NO: 1 or SEQ ID NO: 3 at a target site in the subject, wherein the peptide has binding affinity for fibrous connective tissue-inducing growth factor (GDF), and localization of the GDF by binding to the peptide at the target site stimulates production of fibrous connective tissue.

2. The method of claim 1, wherein the fibrous connective tissue-inducing growth factor is GDF-7.

3. A GDF binding domain comprising a peptide having a sequence at least 95% identical to SEQ ID NO: 1 or SEQ ID NO: 3, or having a sequence with no more than 3 conservative amino acid substitutions in SEQ ID NO: 1 or SEQ ID NO: 3, wherein the binding domain has binding affinity for GDF-7.

4. The GDF binding domain of claim 1, wherein the binding domain is no more than 30 amino acids in length.

5. The GDF binding domain of claim 1, wherein the binding domain is no more than 40 amino acids in length.

6. The GDF binding domain of claim 3, wherein the peptide has at least 97% sequence identity to SEQ ID NO: 1 or SEQ ID NO: 3.

7. An implant comprising a peptide having a sequence at least 95% identical to SEQ ID NO: 1 or SEQ ID NO: 3, or having a sequence with no more than 3 conservative amino acid substitutions in SEQ ID NO: 1 or SEQ ID NO: 3, wherein the peptide has binding affinity for GDF-7.

8. The implant of claim 7, wherein the peptide has a sequence at least 97% identical to SEQ ID NO: 1 or SEQ ID NO: 3.

9. The implant of claim 7, wherein the peptide is no more than 30 amino acids in length.

10. The implant of claim 7, wherein the peptide is no more than 40 amino acids in length.

11. The method of claim 1, wherein the peptide has a sequence at least 97% identical to SEQ ID NO: 1 or SEQ ID NO: 3.

12. The method of claim 1, wherein the peptide is no more than 30 amino acids in length.

13. The method of claim 1, wherein the peptide is no more than 40 amino acids in length.

* * * * *

```
                          SEQUENCE LISTING

<160> NUMBER OF SEQ ID NOS: 79

<210> SEQ ID NO 1
<211> LENGTH: 21
<212> TYPE: PRT
<213> ORGANISM: Artificial
<220> FEATURE:
<223> OTHER INFORMATION: Synthesized

<400> SEQUENCE: 1

Ser Ser Gly Pro Arg Glu Ile Trp Asp Ser Leu Val Gly Val Val Asn
1               5                   10                  15

Pro Gly Trp Ser Arg
            20

<210> SEQ ID NO 2
<211> LENGTH: 21
<212> TYPE: PRT
<213> ORGANISM: Artificial
<220> FEATURE:
<223> OTHER INFORMATION: Synthesized

<400> SEQUENCE: 2

Ser Ser Gly Gly Val Gly Gly Trp Ala Leu Phe Glu Thr Leu Arg Gly
1               5                   10                  15

Lys Glu Val Ser Arg
            20

<210> SEQ ID NO 3
<211> LENGTH: 21
<212> TYPE: PRT
<213> ORGANISM: Artificial
<220> FEATURE:
<223> OTHER INFORMATION: Synthesized

<400> SEQUENCE: 3

Ser Ser Val Ala Glu Trp Ala Leu Arg Ser Trp Glu Gly Met Arg Val
1               5                   10                  15

Gly Glu Ala Ser Arg
            20

<210> SEQ ID NO 4
<211> LENGTH: 21
<212> TYPE: PRT
<213> ORGANISM: Artificial
<220> FEATURE:
<223> OTHER INFORMATION: Synthesized

<400> SEQUENCE: 4

Ser Ser Trp Glu Glu Thr Gly Trp Arg Asp Phe Asn Ser Leu Arg Gly
```

```
1               5                   10                  15
Arg Glu Val Ser Arg
            20

<210> SEQ ID NO 5
<211> LENGTH: 21
<212> TYPE: PRT
<213> ORGANISM: Artificial
<220> FEATURE:
<223> OTHER INFORMATION: Synthesized

<400> SEQUENCE: 5

Ser Arg Glu Ala His Val Gly Trp Gly Val Phe Glu Ala Leu Gln Gly
1               5                   10                  15

Val Thr Val Ser Arg
            20

<210> SEQ ID NO 6
<211> LENGTH: 21
<212> TYPE: PRT
<213> ORGANISM: Artificial
<220> FEATURE:
<223> OTHER INFORMATION: Synthesized

<400> SEQUENCE: 6

Ser Ser Val Gly Trp Asp Glu Phe Met Ser Leu Arg Gly Val Glu Lys
1               5                   10                  15

Lys Gly Trp Ser Arg
            20

<210> SEQ ID NO 7
<211> LENGTH: 21
<212> TYPE: PRT
<213> ORGANISM: Artificial
<220> FEATURE:
<223> OTHER INFORMATION: Synthesized

<400> SEQUENCE: 7

Ser Ser Pro Ser Trp Asp Gln Phe Gln Ser Leu Val Gly Val Pro Thr
1               5                   10                  15

Trp Ala Ala Ser Arg
            20

<210> SEQ ID NO 8
<211> LENGTH: 21
<212> TYPE: PRT
<213> ORGANISM: Artificial
<220> FEATURE:
<223> OTHER INFORMATION: Synthesized

<400> SEQUENCE: 8

Ser Ser Gly Leu Leu Gly Gly Trp Ser Gly Leu Gln Gly Val Glu Leu
1               5                   10                  15

Trp Ser Ser Ser Arg
            20

<210> SEQ ID NO 9
<211> LENGTH: 11
<212> TYPE: PRT
<213> ORGANISM: Artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: X is W, R, or L
```

```
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (4)..(4)
<223> OTHER INFORMATION: X is F or W
<220> FEATURE:
<221> NAME/KEY: MISC_FEATURE
<222> LOCATION: (5)..(5)
<223> OTHER INFORMATION: X is E, D, N, M, Q or S
<220> FEATURE:
<221> NAME/KEY: MISC_FEATURE
<222> LOCATION: (6)..(6)
<223> OTHER INFORMATION: X is S, T, G or A
<220> FEATURE:
<221> NAME/KEY: MISC_FEATURE
<222> LOCATION: (7)..(7)
<223> OTHER INFORMATION: X is L or M
<220> FEATURE:
<221> NAME/KEY: MISC_FEATURE
<222> LOCATION: (8)..(8)
<223> OTHER INFORMATION: X is R, Q or V
<220> FEATURE:
<221> NAME/KEY: MISC_FEATURE
<222> LOCATION: (9)..(9)
<223> OTHER INFORMATION: X is G or V
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is E, V, T or P

<400> SEQUENCE: 9

Xaa Xaa Xaa Xaa Xaa Xaa Xaa Xaa Xaa Xaa Xaa
1               5                   10

<210> SEQ ID NO 10
<211> LENGTH: 11
<212> TYPE: PRT
<213> ORGANISM: Artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: X is W, R or L
<220> FEATURE:
<221> NAME/KEY: MISC_FEATURE
<222> LOCATION: (2)..(2)
<223> OTHER INFORMATION: X is A, E or R
<220> FEATURE:
<221> NAME/KEY: MISC_FEATURE
<222> LOCATION: (3)..(3)
<223> OTHER INFORMATION: X is L, I or S
<220> FEATURE:
<221> NAME/KEY: MISC_FEATURE
<222> LOCATION: (4)..(4)
<223> OTHER INFORMATION: X is F or W
<220> FEATURE:
<221> NAME/KEY: MISC_FEATURE
<222> LOCATION: (5)..(5)
<223> OTHER INFORMATION: X is E, D, N, M, Q or S
<220> FEATURE:
<221> NAME/KEY: MISC_FEATURE
<222> LOCATION: (6)..(6)
<223> OTHER INFORMATION: X is S, T, G or A
<220> FEATURE:
<221> NAME/KEY: MISC_FEATURE
<222> LOCATION: (7)..(7)
<223> OTHER INFORMATION: X is L or M
<220> FEATURE:
<221> NAME/KEY: MISC_FEATURE
<222> LOCATION: (8)..(8)
```

```
<223> OTHER INFORMATION: X is R, Q or V
<220> FEATURE:
<221> NAME/KEY: MISC_FEATURE
<222> LOCATION: (9)..(9)
<223> OTHER INFORMATION: X is G or V
<220> FEATURE:
<221> NAME/KEY: MISC_FEATURE
<222> LOCATION: (10)..(10)
<223> OTHER INFORMATION: X is K, R, V or G
<220> FEATURE:
<221> NAME/KEY: MISC_FEATURE
<222> LOCATION: (11)..(11)
<223> OTHER INFORMATION: X is E, V, T or P

<400> SEQUENCE: 10

Xaa Xaa Xaa Xaa Xaa Xaa Xaa Xaa Xaa Xaa Xaa
1               5                   10

<210> SEQ ID NO 11
<211> LENGTH: 11
<212> TYPE: PRT
<213> ORGANISM: Artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: X is W, R, or L
<220> FEATURE:
<221> NAME/KEY: MISC_FEATURE
<222> LOCATION: (2)..(2)
<223> OTHER INFORMATION: X is A, E or R
<220> FEATURE:
<221> NAME/KEY: MISC_FEATURE
<222> LOCATION: (3)..(3)
<223> OTHER INFORMATION: X is L, I or S
<220> FEATURE:
<221> NAME/KEY: MISC_FEATURE
<222> LOCATION: (4)..(4)
<223> OTHER INFORMATION: X is F or W
<220> FEATURE:
<221> NAME/KEY: MISC_FEATURE
<222> LOCATION: (5)..(5)
<223> OTHER INFORMATION: X is E or D
<220> FEATURE:
<221> NAME/KEY: MISC_FEATURE
<222> LOCATION: (6)..(6)
<223> OTHER INFORMATION: X is S, T or G
<220> FEATURE:
<221> NAME/KEY: MISC_FEATURE
<222> LOCATION: (7)..(7)
<223> OTHER INFORMATION: X is L or M
<220> FEATURE:
<221> NAME/KEY: MISC_FEATURE
<222> LOCATION: (8)..(8)
<223> OTHER INFORMATION: X is R or V
<220> FEATURE:
<221> NAME/KEY: MISC_FEATURE
<222> LOCATION: (9)..(9)
<223> OTHER INFORMATION: X is G or V
<220> FEATURE:
<221> NAME/KEY: MISC_FEATURE
<222> LOCATION: (10)..(10)
<223> OTHER INFORMATION: X is K, V or G
<220> FEATURE:
<221> NAME/KEY: MISC_FEATURE
<222> LOCATION: (11)..(11)
<223> OTHER INFORMATION: X is E or V

<400> SEQUENCE: 11

Xaa Xaa Xaa Xaa Xaa Xaa Xaa Xaa Xaa Xaa Xaa
1               5                   10

<210> SEQ ID NO 12
<211> LENGTH: 12
<212> TYPE: PRT
```

```
<213> ORGANISM: Artificial
<220> FEATURE:
<223> OTHER INFORMATION: Synthesized
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (6)..(6)
<223> OTHER INFORMATION: X is S or T
<220> FEATURE:
<221> NAME/KEY: MISC_FEATURE
<222> LOCATION: (8)..(8)
<223> OTHER INFORMATION: X is any amino acid
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (12)..(12)
<223> OTHER INFORMATION: X is any amino acid

<400> SEQUENCE: 12

Trp Xaa Xaa Phe Glu Xaa Leu Xaa Gly Xaa Glu Xaa
1               5                   10

<210> SEQ ID NO 13
<211> LENGTH: 13
<212> TYPE: PRT
<213> ORGANISM: Artificial
<220> FEATURE:
<223> OTHER INFORMATION: Synthesized

<400> SEQUENCE: 13

Phe Leu Ser Phe Val Phe Pro Ala Ser Ala Trp Gly Gly
1               5                   10

<210> SEQ ID NO 14
<211> LENGTH: 13
<212> TYPE: PRT
<213> ORGANISM: Artificial
<220> FEATURE:
<223> OTHER INFORMATION: Synthesized

<400> SEQUENCE: 14

Phe Tyr Met Pro Phe Gly Pro Thr Trp Trp Gln His Val
1               5                   10

<210> SEQ ID NO 15
<211> LENGTH: 13
<212> TYPE: PRT
<213> ORGANISM: Artificial
<220> FEATURE:
<223> OTHER INFORMATION: Synthesized

<400> SEQUENCE: 15

Leu Phe Ser Trp Phe Leu Pro Thr Asp Asn Tyr Pro Val
1               5                   10

<210> SEQ ID NO 16
<211> LENGTH: 13
<212> TYPE: PRT
<213> ORGANISM: Artificial
<220> FEATURE:
<223> OTHER INFORMATION: Synthesized

<400> SEQUENCE: 16

Phe Met Asp Ile Trp Ser Pro Trp His Leu Leu Gly Thr
1               5                   10
```

```
<210> SEQ ID NO 17
<211> LENGTH: 13
<212> TYPE: PRT
<213> ORGANISM: Artificial
<220> FEATURE:
<223> OTHER INFORMATION: Synthesized

<400> SEQUENCE: 17

Phe Ser Ser Leu Phe Phe Pro His Trp Pro Ala Gln Leu
1               5                   10

<210> SEQ ID NO 18
<211> LENGTH: 19
<212> TYPE: PRT
<213> ORGANISM: Artificial
<220> FEATURE:
<223> OTHER INFORMATION: Synthesized

<400> SEQUENCE: 18

Ser Cys Ala Met Ala Gln Trp Phe Cys Asp Arg Ala Glu Pro His His
1               5                   10                  15

Val Ile Ser

<210> SEQ ID NO 19
<211> LENGTH: 19
<212> TYPE: PRT
<213> ORGANISM: Artificial
<220> FEATURE:
<223> OTHER INFORMATION: Synthesized

<400> SEQUENCE: 19

Ser Cys Asn Met Ser His Leu Thr Gly Val Ser Leu Cys Asp Ser Leu
1               5                   10                  15

Ala Thr Ser

<210> SEQ ID NO 20
<211> LENGTH: 19
<212> TYPE: PRT
<213> ORGANISM: Artificial
<220> FEATURE:
<223> OTHER INFORMATION: Synthesized

<400> SEQUENCE: 20

Ser Cys Val Tyr Ser Phe Ile Asp Gly Ser Gly Cys Asn Ser His Ser
1               5                   10                  15

Leu Gly Ser

<210> SEQ ID NO 21
<211> LENGTH: 19
<212> TYPE: PRT
<213> ORGANISM: Artificial
<220> FEATURE:
<223> OTHER INFORMATION: Synthesized

<400> SEQUENCE: 21

Ser Cys Ser Gly Phe His Leu Leu Cys Glu Ser Arg Ser Met Gln Arg
1               5                   10                  15

Glu Leu Ser

<210> SEQ ID NO 22
<211> LENGTH: 19
<212> TYPE: PRT
<213> ORGANISM: Artificial
<220> FEATURE:
```

-continued

<223> OTHER INFORMATION: Synthesized

<400> SEQUENCE: 22

Ser Cys Gly Ile Leu Cys Ser Ala Phe Pro Phe Asn Asn His Gln Val
1               5                   10                  15

Gly Ala Ser

<210> SEQ ID NO 23
<211> LENGTH: 19
<212> TYPE: PRT
<213> ORGANISM: Artificial
<220> FEATURE:
<223> OTHER INFORMATION: Synthesized

<400> SEQUENCE: 23

Ser Cys Cys Ser Met Phe Phe Lys Asn Val Ser Tyr Val Gly Ala Ser
1               5                   10                  15

Asn Pro Ser

<210> SEQ ID NO 24
<211> LENGTH: 19
<212> TYPE: PRT
<213> ORGANISM: Artificial
<220> FEATURE:
<223> OTHER INFORMATION: Synthesized

<400> SEQUENCE: 24

Ser Cys Pro Ile Trp Lys Tyr Cys Asp Asp Tyr Ser Arg Ser Gly Ser
1               5                   10                  15

Ile Phe Ser

<210> SEQ ID NO 25
<211> LENGTH: 18
<212> TYPE: PRT
<213> ORGANISM: Artificial
<220> FEATURE:
<223> OTHER INFORMATION: Synthesized

<400> SEQUENCE: 25

Ser Cys Leu Phe Asn Ser Met Lys Cys Leu Val Leu Ile Leu Cys Phe
1               5                   10                  15

Val Ser

<210> SEQ ID NO 26
<211> LENGTH: 19
<212> TYPE: PRT
<213> ORGANISM: Artificial
<220> FEATURE:
<223> OTHER INFORMATION: Synthesized

<400> SEQUENCE: 26

Ser Cys Tyr Val Asn Gly His Asn Ser Val Trp Val Val Phe Trp
1               5                   10                  15

Gly Val Ser

<210> SEQ ID NO 27
<211> LENGTH: 19
<212> TYPE: PRT
<213> ORGANISM: Artificial
<220> FEATURE:
<223> OTHER INFORMATION: Synthesized

<400> SEQUENCE: 27

Ser Cys Asp Phe Val Cys Asn Val Leu Phe Asn Val Asn His Gly Ser

```
                 1               5                  10                 15
Asn Met Ser

<210> SEQ ID NO 28
<211> LENGTH: 19
<212> TYPE: PRT
<213> ORGANISM: Artificial
<220> FEATURE:
<223> OTHER INFORMATION: Synthesized

<400> SEQUENCE: 28

Ser Cys Leu Asn Lys Phe Phe Val Leu Met Ser Val Gly Leu Arg Ser
1               5                   10                  15

Tyr Thr Ser

<210> SEQ ID NO 29
<211> LENGTH: 19
<212> TYPE: PRT
<213> ORGANISM: Artificial
<220> FEATURE:
<223> OTHER INFORMATION: Synthesized

<400> SEQUENCE: 29

Ser Cys Cys Asn His Asn Ser Thr Ser Val Lys Asp Val Gln Phe Pro
1               5                   10                  15

Thr Leu Ser

<210> SEQ ID NO 30
<211> LENGTH: 13
<212> TYPE: PRT
<213> ORGANISM: Artificial
<220> FEATURE:
<223> OTHER INFORMATION: Synthesized

<400> SEQUENCE: 30

Phe Phe Pro Ser Ser Trp Tyr Ser His Leu Gly Val Leu
1               5                   10

<210> SEQ ID NO 31
<211> LENGTH: 13
<212> TYPE: PRT
<213> ORGANISM: Artificial
<220> FEATURE:
<223> OTHER INFORMATION: Synthesized

<400> SEQUENCE: 31

Phe Phe Gly Phe Asp Val Tyr Asp Met Ser Asn Ala Leu
1               5                   10

<210> SEQ ID NO 32
<211> LENGTH: 13
<212> TYPE: PRT
<213> ORGANISM: Artificial
<220> FEATURE:
<223> OTHER INFORMATION: Synthesized

<400> SEQUENCE: 32

Leu Ser Phe Ser Asp Phe Tyr Phe Ser Glu Gly Ser Glu
1               5                   10

<210> SEQ ID NO 33
<211> LENGTH: 13
<212> TYPE: PRT
<213> ORGANISM: Artificial
<220> FEATURE:
<223> OTHER INFORMATION: Synthesized
```

-continued

```
<400> SEQUENCE: 33

Phe Ser Tyr Ser Val Ser Tyr Ala His Pro Glu Gly Leu
1               5                   10

<210> SEQ ID NO 34
<211> LENGTH: 13
<212> TYPE: PRT
<213> ORGANISM: Artificial
<220> FEATURE:
<223> OTHER INFORMATION: Synthesized

<400> SEQUENCE: 34

Leu Pro His Leu Ile Gln Tyr Arg Val Leu Leu Val Ser
1               5                   10

<210> SEQ ID NO 35
<211> LENGTH: 19
<212> TYPE: PRT
<213> ORGANISM: Artificial
<220> FEATURE:
<223> OTHER INFORMATION: Synthesized

<400> SEQUENCE: 35

Ser Cys Tyr Val Asn Gly His Asn Ser Val Trp Val Val Phe Trp
1               5                   10                  15

Gly Val Ser

<210> SEQ ID NO 36
<211> LENGTH: 19
<212> TYPE: PRT
<213> ORGANISM: Artificial
<220> FEATURE:
<223> OTHER INFORMATION: Synthesized

<400> SEQUENCE: 36

Ser Cys Asn Ser Phe Met Phe Ile Asn Gly Ser Phe Lys Glu Thr Gly
1               5                   10                  15

Gly Cys Ser

<210> SEQ ID NO 37
<211> LENGTH: 19
<212> TYPE: PRT
<213> ORGANISM: Artificial
<220> FEATURE:
<223> OTHER INFORMATION: Synthesized

<400> SEQUENCE: 37

Ser Cys Phe Gly Asn Leu Gly Asn Leu Ile Tyr Thr Cys Asp Arg Leu
1               5                   10                  15

Met Pro Ser

<210> SEQ ID NO 38
<211> LENGTH: 19
<212> TYPE: PRT
<213> ORGANISM: Artificial
<220> FEATURE:
<223> OTHER INFORMATION: Synthesized

<400> SEQUENCE: 38

Ser Cys Ser Phe Phe Met Pro Trp Cys Asn Phe Leu Asn Gly Glu Met
1               5                   10                  15

Ala Val Ser
```

```
<210> SEQ ID NO 39
<211> LENGTH: 19
<212> TYPE: PRT
<213> ORGANISM: Artificial
<220> FEATURE:
<223> OTHER INFORMATION: Synthesized

<400> SEQUENCE: 39

Ser Cys Phe Gly Asn Val Phe Cys Val Tyr Asn Gln Phe Ala Ala Gly
1               5                   10                  15

Leu Phe Ser

<210> SEQ ID NO 40
<211> LENGTH: 19
<212> TYPE: PRT
<213> ORGANISM: Artificial
<220> FEATURE:
<223> OTHER INFORMATION: Synthesized

<400> SEQUENCE: 40

Ser Cys Cys Phe Ile Asn Ser Asn Phe Ser Val Met Asn His Ser Leu
1               5                   10                  15

Phe Lys Ser

<210> SEQ ID NO 41
<211> LENGTH: 19
<212> TYPE: PRT
<213> ORGANISM: Artificial
<220> FEATURE:
<223> OTHER INFORMATION: Synthesized

<400> SEQUENCE: 41

Ser Cys Asp Tyr Phe Ser Phe Leu Glu Cys Phe Ser Asn Gly Trp Ser
1               5                   10                  15

Gly Ala Ser

<210> SEQ ID NO 42
<211> LENGTH: 19
<212> TYPE: PRT
<213> ORGANISM: Artificial
<220> FEATURE:
<223> OTHER INFORMATION: Synthesized

<400> SEQUENCE: 42

Ser Cys Trp Met Gly Leu Phe Glu Cys Pro Asp Ala Trp Leu His Asp
1               5                   10                  15

Trp Asp Ser

<210> SEQ ID NO 43
<211> LENGTH: 19
<212> TYPE: PRT
<213> ORGANISM: Artificial
<220> FEATURE:
<223> OTHER INFORMATION: Synthesized

<400> SEQUENCE: 43

Ser Cys Phe Trp Tyr Ser Trp Leu Cys Ser Ala Ser Ser Ser Asp Ala
1               5                   10                  15

Leu Ile Ser

<210> SEQ ID NO 44
<211> LENGTH: 19
<212> TYPE: PRT
<213> ORGANISM: Artificial
<220> FEATURE:
```

```
<223> OTHER INFORMATION: Synthesized

<400> SEQUENCE: 44

Ser Cys Phe Gly Asn Phe Leu Ser Phe Gly Phe Asn Cys Glu Ser Ala
1               5                   10                  15

Leu Gly Ser

<210> SEQ ID NO 45
<211> LENGTH: 19
<212> TYPE: PRT
<213> ORGANISM: Artificial
<220> FEATURE:
<223> OTHER INFORMATION: Synthesized

<400> SEQUENCE: 45

Ser Cys Leu Tyr Cys His Leu Asn Asn Gln Phe Leu Ser Trp Val Ser
1               5                   10                  15

Gly Asn Ser

<210> SEQ ID NO 46
<211> LENGTH: 19
<212> TYPE: PRT
<213> ORGANISM: Artificial
<220> FEATURE:
<223> OTHER INFORMATION: Synthesized

<400> SEQUENCE: 46

Ser Cys Phe Gly Phe Ser Asp Cys Leu Ser Trp Phe Val Gln Pro Ser
1               5                   10                  15

Thr Ala Ser

<210> SEQ ID NO 47
<211> LENGTH: 19
<212> TYPE: PRT
<213> ORGANISM: Artificial
<220> FEATURE:
<223> OTHER INFORMATION: Synthesized

<400> SEQUENCE: 47

Ser Cys Asn His Leu Gly Phe Phe Ser Ser Phe Cys Asp Arg Leu Val
1               5                   10                  15

Glu Asn Ser

<210> SEQ ID NO 48
<211> LENGTH: 19
<212> TYPE: PRT
<213> ORGANISM: Artificial
<220> FEATURE:
<223> OTHER INFORMATION: Synthesized

<400> SEQUENCE: 48

Ser Cys Gly Tyr Phe Cys Ser Phe Tyr Asn Tyr Leu Asp Ile Gly Thr
1               5                   10                  15

Ala Ser Ser

<210> SEQ ID NO 49
<211> LENGTH: 19
<212> TYPE: PRT
<213> ORGANISM: Artificial
<220> FEATURE:
<223> OTHER INFORMATION: Synthesized

<400> SEQUENCE: 49

Ser Cys Asn Ser Ser Ser Tyr Ser Trp Tyr Cys Trp Phe Gly Gly Ser
```

```
1               5                  10                 15
Ser Pro Ser

<210> SEQ ID NO 50
<211> LENGTH: 13
<212> TYPE: PRT
<213> ORGANISM: Artificial
<220> FEATURE:
<223> OTHER INFORMATION: Synthesized

<400> SEQUENCE: 50

Phe Gly His Gly Trp Leu Asn Thr Leu Asn Leu Gly Trp
1               5                  10

<210> SEQ ID NO 51
<211> LENGTH: 13
<212> TYPE: PRT
<213> ORGANISM: Artificial
<220> FEATURE:
<223> OTHER INFORMATION: Synthesized

<400> SEQUENCE: 51

Phe Ser Pro Phe Ser Ala Asn Leu Trp Tyr Asp Met Phe
1               5                  10

<210> SEQ ID NO 52
<211> LENGTH: 13
<212> TYPE: PRT
<213> ORGANISM: Artificial
<220> FEATURE:
<223> OTHER INFORMATION: Synthesized

<400> SEQUENCE: 52

Val Phe Val Pro Phe Gly Asn Trp Leu Ser Thr Ser Val
1               5                  10

<210> SEQ ID NO 53
<211> LENGTH: 13
<212> TYPE: PRT
<213> ORGANISM: Artificial
<220> FEATURE:
<223> OTHER INFORMATION: Synthesized

<400> SEQUENCE: 53

Phe Trp Asn Val Asn Tyr Asn Pro Trp Gly Trp Asn Tyr
1               5                  10

<210> SEQ ID NO 54
<211> LENGTH: 13
<212> TYPE: PRT
<213> ORGANISM: Artificial
<220> FEATURE:
<223> OTHER INFORMATION: Synthesized

<400> SEQUENCE: 54

Phe Tyr Trp Asp Arg Leu Asn Val Gly Trp Gly Leu Leu
1               5                  10

<210> SEQ ID NO 55
<211> LENGTH: 13
<212> TYPE: PRT
<213> ORGANISM: Artificial
<220> FEATURE:
<223> OTHER INFORMATION: Synthesized

<400> SEQUENCE: 55

Leu Tyr Ser Thr Met Tyr Pro Gly Met Ser Trp Leu Val
```

```
1               5                   10
```

<210> SEQ ID NO 56
<211> LENGTH: 19
<212> TYPE: PRT
<213> ORGANISM: Artificial
<220> FEATURE:
<223> OTHER INFORMATION: Synthesized

<400> SEQUENCE: 56

```
Ser Cys Phe Tyr Gln Asn Val Ile Ser Ser Phe Ala Gly Asn Pro
1               5                   10                  15

Trp Glu Cys
```

<210> SEQ ID NO 57
<211> LENGTH: 19
<212> TYPE: PRT
<213> ORGANISM: Artificial
<220> FEATURE:
<223> OTHER INFORMATION: Synthesized

<400> SEQUENCE: 57

```
Ser Cys Asn Met Leu Leu Asn Ser Leu Pro Leu Pro Ser Glu Asp Trp
1               5                   10                  15

Ser Ala Cys
```

<210> SEQ ID NO 58
<211> LENGTH: 19
<212> TYPE: PRT
<213> ORGANISM: Artificial
<220> FEATURE:
<223> OTHER INFORMATION: Synthesized

<400> SEQUENCE: 58

```
Ser Cys Pro Phe Thr His Ser Leu Ala Leu Asn Thr Asp Arg Ala Ser
1               5                   10                  15

Pro Gly Cys
```

<210> SEQ ID NO 59
<211> LENGTH: 19
<212> TYPE: PRT
<213> ORGANISM: Artificial
<220> FEATURE:
<223> OTHER INFORMATION: Synthesized

<400> SEQUENCE: 59

```
Ser Cys Phe Glu Ser Asp Phe Pro Asn Val Arg His His Val Leu Lys
1               5                   10                  15

Gln Ser Cys
```

<210> SEQ ID NO 60
<211> LENGTH: 19
<212> TYPE: PRT
<213> ORGANISM: Artificial
<220> FEATURE:
<223> OTHER INFORMATION: Synthesized

<400> SEQUENCE: 60

```
Ser Cys Val Phe Asp Ser Lys His Phe Ser Pro Thr His Ser Pro His
1               5                   10                  15

Asp Val Cys
```

<210> SEQ ID NO 61
<211> LENGTH: 19

```
<212> TYPE: PRT
<213> ORGANISM: Artificial
<220> FEATURE:
<223> OTHER INFORMATION: Synthesized

<400> SEQUENCE: 61

Ser Cys Gly Asp His Met Thr Asp Lys Asn Met Pro Asn Ser Gly Ile
1               5                   10                  15

Ser Gly Cys

<210> SEQ ID NO 62
<211> LENGTH: 19
<212> TYPE: PRT
<213> ORGANISM: Artificial
<220> FEATURE:
<223> OTHER INFORMATION: Synthesized

<400> SEQUENCE: 62

Ser Cys Asp Phe Phe Asn Arg His Gly Tyr Asn Ser Gly Cys Glu His
1               5                   10                  15

Ser Val Cys

<210> SEQ ID NO 63
<211> LENGTH: 19
<212> TYPE: PRT
<213> ORGANISM: Artificial
<220> FEATURE:
<223> OTHER INFORMATION: Synthesized

<400> SEQUENCE: 63

Ser Cys Gly Asp His Met Thr Asp Lys Asn Met Pro Asn Ser Gly Ile
1               5                   10                  15

Ser Gly Cys

<210> SEQ ID NO 64
<211> LENGTH: 19
<212> TYPE: PRT
<213> ORGANISM: Artificial
<220> FEATURE:
<223> OTHER INFORMATION: Synthesized

<400> SEQUENCE: 64

Ser Cys Tyr Tyr Asn Gly Leu Val Val His His Ser Asn Ser Gly His
1               5                   10                  15

Lys Asp Cys

<210> SEQ ID NO 65
<211> LENGTH: 18
<212> TYPE: PRT
<213> ORGANISM: Artificial
<220> FEATURE:
<223> OTHER INFORMATION: Synthesized

<400> SEQUENCE: 65

Cys Trp Ser Arg Phe Arg Leu Phe Met Leu Phe Cys Met Phe Tyr Leu
1               5                   10                  15

Val Ser

<210> SEQ ID NO 66
<211> LENGTH: 18
<212> TYPE: PRT
<213> ORGANISM: Artificial
<220> FEATURE:
<223> OTHER INFORMATION: Synthesized
```

```
<400> SEQUENCE: 66

Cys Ile Lys Tyr Pro Phe Leu Tyr Cys Cys Leu Leu Ser Leu Phe Leu
1               5                   10                  15

Phe Ser

<210> SEQ ID NO 67
<211> LENGTH: 16
<212> TYPE: PRT
<213> ORGANISM: Artificial
<220> FEATURE:
<223> OTHER INFORMATION: Synthesized

<400> SEQUENCE: 67

Ser Trp Trp Gly Phe Trp Asn Gly Ser Ala Ala Pro Val Trp Ser Arg
1               5                   10                  15

<210> SEQ ID NO 68
<211> LENGTH: 20
<212> TYPE: PRT
<213> ORGANISM: Artificial
<220> FEATURE:
<223> OTHER INFORMATION: Synthesized

<400> SEQUENCE: 68

Ser Trp Asp Phe Arg Ser Leu Arg Asp Trp Trp Pro Pro Ala Pro Ser
1               5                   10                  15

Leu Ser Ser Arg
            20

<210> SEQ ID NO 69
<211> LENGTH: 16
<212> TYPE: PRT
<213> ORGANISM: Artificial
<220> FEATURE:
<223> OTHER INFORMATION: Synthesized

<400> SEQUENCE: 69

Ser Ile Phe Ser Thr Trp Asn Pro Trp Ser Pro Tyr Ser Val Ser Arg
1               5                   10                  15

<210> SEQ ID NO 70
<211> LENGTH: 15
<212> TYPE: PRT
<213> ORGANISM: Artificial
<220> FEATURE:
<223> OTHER INFORMATION: Synthesized

<400> SEQUENCE: 70

Ser Phe Gly Ser Trp Trp Gly Ser Gly Ala Ala Ser Ser Arg
1               5                   10                  15

<210> SEQ ID NO 71
<211> LENGTH: 17
<212> TYPE: PRT
<213> ORGANISM: Artificial
<220> FEATURE:
<223> OTHER INFORMATION: Synthesized

<400> SEQUENCE: 71

Tyr Phe Arg Ala Phe Arg Lys Phe Val Lys Pro Phe Lys Arg Ala Phe
1               5                   10                  15

Lys

<210> SEQ ID NO 72
<211> LENGTH: 5
```

```
<212> TYPE: PRT
<213> ORGANISM: Artificial
<220> FEATURE:
<223> OTHER INFORMATION: Synthesized

<400> SEQUENCE: 72

Gly Ser Ser Gly Lys
1               5

<210> SEQ ID NO 73
<211> LENGTH: 26
<212> TYPE: PRT
<213> ORGANISM: Artificial
<220> FEATURE:
<223> OTHER INFORMATION: Synthesized

<400> SEQUENCE: 73

Ser Ser Gly Pro Arg Glu Ile Trp Asp Ser Leu Val Gly Val Val Asn
1               5                   10                  15
Pro Gly Trp Ser Arg Gly Ser Ser Gly Lys
            20                  25

<210> SEQ ID NO 74
<211> LENGTH: 26
<212> TYPE: PRT
<213> ORGANISM: Artificial
<220> FEATURE:
<223> OTHER INFORMATION: Synthesized

<400> SEQUENCE: 74

Ser Ser Gly Gly Val Gly Gly Trp Ala Leu Phe Glu Thr Leu Arg Gly
1               5                   10                  15
Lys Glu Val Ser Arg Gly Ser Ser Gly Lys
            20                  25

<210> SEQ ID NO 75
<211> LENGTH: 26
<212> TYPE: PRT
<213> ORGANISM: Artificial
<220> FEATURE:
<223> OTHER INFORMATION: Synthesized

<400> SEQUENCE: 75

Ser Ser Val Ala Glu Trp Ala Leu Arg Ser Trp Glu Gly Met Arg Val
1               5                   10                  15
Gly Glu Ala Ser Arg Gly Ser Ser Gly Lys
            20                  25

<210> SEQ ID NO 76
<211> LENGTH: 21
<212> TYPE: PRT
<213> ORGANISM: Artificial
<220> FEATURE:
<223> OTHER INFORMATION: Synthesized

<400> SEQUENCE: 76

Ser Trp Trp Gly Phe Trp Asn Gly Ser Ala Ala Pro Val Trp Ser Arg
1               5                   10                  15
Gly Ser Ser Gly Lys
            20

<210> SEQ ID NO 77
<211> LENGTH: 93
<212> TYPE: DNA
<213> ORGANISM: Artificial
<220> FEATURE:
```

```
<223> OTHER INFORMATION: Synthesized

<400> SEQUENCE: 77
tcgagtgggc cgagggagat ttgggatagt ttggttggtg tggtgaatcc ggggtggtct      60
agaggttacc catacgacgt cccagactac gct                                  93

<210> SEQ ID NO 78
<211> LENGTH: 93
<212> TYPE: DNA
<213> ORGANISM: Artificial
<220> FEATURE:
<223> OTHER INFORMATION: Synthesized

<400> SEQUENCE: 78
tcgagcggtg gtgttggtgg gtgggcgttg tttgagactc tgcgtggtaa ggaggtgtct      60
agaggttacc catacgacgt cccagactac gct                                  93

<210> SEQ ID NO 79
<211> LENGTH: 96
<212> TYPE: DNA
<213> ORGANISM: Artificial
<220> FEATURE:
<223> OTHER INFORMATION: Synthesized

<400> SEQUENCE: 79
tcgagcgttg ctgagtgggc tttgaggagt tgggagggca tgcgggttgg ggaggcgtct      60
agaggttacc catacgacgt cccagactac gctggg                               96
```